(12) United States Patent
Maszewska et al.

(10) Patent No.: US 10,435,671 B2
(45) Date of Patent: Oct. 8, 2019

(54) BACTERIOPHAGE STRAINS AGAINST PROTEUS MIRABILIS AND USE THEREOF

(71) Applicant: UNIWERSYTET LODZKI, Lodz (PL)

(72) Inventors: Agnieszka Maszewska, Lodz (PL); Antoni Rozalski, Lodz (PL)

(73) Assignee: UNIWERSYTET LODZKI, Lodz (PL)

( * ) Notice: Subject to any disclaimer, the term of this patent is extended or adjusted under 35 U.S.C. 154(b) by 0 days.

(21) Appl. No.: 15/742,127

(22) PCT Filed: Jul. 7, 2016

(86) PCT No.: PCT/IB2016/000974
§ 371 (c)(1),
(2) Date: Jan. 5, 2018

(87) PCT Pub. No.: WO2017/006175
PCT Pub. Date: Jan. 12, 2017

(65) Prior Publication Data
US 2019/0032022 A1  Jan. 31, 2019

(30) Foreign Application Priority Data

Jul. 7, 2015 (PL) .......................................... 413054

(51) Int. Cl.
| | | |
|---|---|---|
| *C12N 7/00* | (2006.01) | |
| *A61P 31/04* | (2006.01) | |
| *A01N 63/00* | (2006.01) | |
| *A61K 35/76* | (2015.01) | |
| *A61K 39/00* | (2006.01) | |

(52) U.S. Cl.
CPC .............. *C12N 7/00* (2013.01); *A01N 63/00* (2013.01); *A61K 35/76* (2013.01); *A61P 31/04* (2018.01); *A61K 39/00* (2013.01); *C12N 2795/00021* (2013.01); *C12N 2795/00031* (2013.01); *C12N 2795/00032* (2013.01)

(58) Field of Classification Search
None
See application file for complete search history.

(56) References Cited

PUBLICATIONS

Susan M. Lehman et al., "Bacteriophage-Mediated Control of a Two-Species Biofilm Formed by Microorganisms Causing Catheter-Associated Urinary Tract Infections in an In Vitro Urinary Catheter Model," Antimicrobial Agents and Chemotherapy, vol. 59, No. 2, Feb. 1, 2015 (Feb. 1, 2015), pp. 1127-113.

Louise Carson, et al., "The use of lytic bacteriophages in the prevention and eradication of biofilms of Proteus mirabilis and Escherichia coli," FEMS Immunology and Medical Microbiology, vol. 59, No. 3, Aug. 1, 2010 (Aug. 1, 2010), pp. 447-455.

G. Hitch, et al., "Isolation of bacteriophages from the oral cavity," Letters in Applied Microbiology, vol. 39, No. 2, Aug. 1, 2004 (Aug. 1, 2004), pp. 215-219.

B. Weber-Dabrowska, "Bacteriophages as an efficient therapy for antibiotic-resistant septicemia in man," Transplantation Proceedings, vol. 35, No. 4, Jun. 1, 2003 (Jun. 1, 2003), pp. 1385-1386.

Sylwia Parasion, et al., "Bacteriophages as an alternative strategy for fighting biofilm development," Polish journal of microbiology, Jan. 1, 2014 (Jan. 1, 2014), pp. 137-145.

Moryl Magdalena, et al., "Analysis of Proteus mirabilis Distribution in Multi-Species Biofilms on Urinary Catheters and Determination of Bacteria Resistance to Antimicrobial Agents," Polish journal of microbiology, vol. 62, No. 4, Jan. 1, 2013 (Jan. 1, 2013), pp. 377-384.

Weiling Fu, et al, "Bacteriophage cocktail for the prevention of biofilm formation by Pseudomonas aeruginosa on catheters in an in vitro model system," Antimicrobial Agens and Chemotherapy, vol. 54, No. 1, Jan. 1, 2010 (Jan. 1, 2010), pp. 397-404.

*Primary Examiner* — Nicole Kinsey White
(74) *Attorney, Agent, or Firm* — Arrigo, Lee, Guttman & Mouta-Bellum LLP

(57) ABSTRACT

The invention covers new bacteriophage strains specific against bacteria belonging to the species *Proteus mirabilis*, deposited with the Polish Collection of Microorganisms (PCM) under the access numbers: F/00084 (72APm5211), F/00085 (39APmC32), F/00086 (65APm2833), for use for use in the prophylaxis and therapy. In accordance with the invention the above mentioned bacteriophage strains, in form of complete particles of the single bacteriophage strain, in form of bacteriophage lysates, optionally in form of purified bacteriophage proteins, in particular lytic enzymes that degrade the bacterial cell wall and enzymes that decompose bacterial extracellular polysaccharides, are intended for use in therapy as anti-bacterial agents, in particular against bacteria of the species *Proteus mirabilis*, especially the drug- and multidrug-resistant strains of the species, advantageously in urinary tract infections. In accordance with the invention the above mentioned bacteriophage strains, in form of a cocktail comprising two or more active bacteriophages, in form of lysates of two or more active bacteriophages, optionally in form of purified bacteriophage proteins of two or more active bacteriophages, especially lytic enzymes that degrade the bacterial cell wall and enzymes that decompose bacterial extracellular polysaccharides, are intended for use in therapy as anti-bacterial agents, in particular against bacteria of the species *Proteus mirabilis*, especially the drug- and multidrug-resistant strains of the species, advantageously in urinary tract infections. The manufactured preparations or compositions are in gel or liquid form and are intended for use in combination or in composition with other anti-bacterial agent, or with other medicaments, wherein the liquid form may be used spray, compresses, rinse/wash liquid preparation or wet compresses.

20 Claims, 16 Drawing Sheets

| Phages | Plaque morphology | |
|---|---|---|
| | diameter [mm] | halo [mm] |
| 39A PmC32 | 3 ir* | 5 |
| 65A Pm2833 | 1 | - |
| 72A Pm5211 | 4 ir | 3 |
| 28 PmC5 | 0.5 | - |
| 29 PmC6 | 3 | <1 |
| 30 PmC7 | 3 | <1 |
| 31 PmC8 | 0.5 | - |
| 32 PmC9 | 1 | - |
| 34 PmC12 | 0.5 | - |
| 35 PmC15 | 1 | - |
| 36 PmC20 | 4 | <1 |
| 36A PmC20 | 4 | <1 |
| 36B PmC20 | 5 | 1 |
| 36C PmC20 | 2 | <1 |
| 36D PmC20 | 2 | <1 |
| 37A PmC24 | 0.5 | - |
| 38 PmC31 | 1 | - |
| 40A PmC33 | 5 | <1 |
| 44 PmC46 | 0.5 | - |
| 45 PmC57 | 1 | - |
| 46 PmC70 | 4 ir | 2 |
| 49 PmC84 | 1 | - |
| 49A PmC84 | 8 | 2 |
| 52 Pm484 | 2 | <1 |
| 53A Pm512 | 0.5 | 1 |
| 54A Pm677 | 3 | - |
| 56 Pm942 | 2 | 3 |
| 56A Pm942 | 4 | <1 |
| 58 Pm1220 | 3 | - |
| 58A Pm1220 | 6 | 1 |
| 58B Pm1220 | 6 | - |
| 58C Pm1220 | 5 | - |
| 61 Pm1683 | 0.5 | - |
| 62 Pm1984 | 2 ir | 1 |
| 64 Pm2733 | 2 | <1 |
| 65 Pm2833 | 2 | <1 |
| 65B Pm2833 | 1, turbid | - |
| 66 Pm2867 | 1 ir | - |
| 66A Pm2867 | 3 ir | - |
| 68 Pm3907 | 3 | - |
| 68B Pm3907 | 4 ir, turbid | <1 |
| 70 Pm4490 | 3 ir | 3 |
| 70A Pm4490 | 2 ir | <1 |
| 71 Pm4955 | 5 ir | - |
| 71A Pm4955 | 2 ir | 2 |
| 72 Pm5211 | 5 | 1 |
| 72B Pm5211 | 3 ir | - |
| 75 PmI090 | 1 | <1 |

* ir - irregular shape of plaque

FIG. 7

■ - COMPLETELY LYSED BACTERIA
☐ - ALMOST CLAR SPOT (WEAK BACTERIAL GROWTH)
▩ - MEDIUM TURBID SPOT (THE MEAN BACTERIAL GROWTH)

*P. MIRABILIS STRAINS — % OF BIOFILM DESTRUCTION*

| PHAGES | C5 Z | C5 SD | C6 Z | C6 SD | C7 Z | C7 SD | C8 Z | C8 SD | C9 Z | C9 SD | C11 Z | C11 SD | C12 Z | C12 SD | C15 Z | C15 SD | C20 Z | C20 SD | C24 Z | C24 SD | C31 Z | C31 SD | C32 Z | C32 SD | C33 Z | C33 SD | C34 Z | C34 SD | C41 Z | C41 SD | C44 Z | C44 SD | C46 Z | C46 SD | C57 Z | C57 SD |
|---|---|---|---|---|---|---|---|---|---|---|---|---|---|---|---|---|---|---|---|---|---|---|---|---|---|---|---|---|---|---|---|---|---|---|---|---|
| 39APmC32 | 59 | 13 | 78 | 15 | 79 | 11 | 45 | 22 | 68 | 10 | 25 | 24 | 38 | 22 | 51 | 23 | 8 | 10 | 10 | 10 | 25 | 22 | 52 | 16 | 64 | 10 | 33 | 20 | 73 | 7 | 7 | 7 | 61 | 22 | 4 | 2 |
| 65APm2833 | 10 | 10 | 39 | 33 | 41 | 26 | 3 | 8 | 38 | 18 | 6 | 8 | -3 | 15 | 11 | 25 | -3 | 3 | -8 | 2 | -6 | 13 | 50 | 19 | 19 | 15 | 56 | 12 | 57 | 21 | 43 | 32 | 1 | 9 | -1 | 3 |
| 72APm5211 | 39 | 29 | 25 | 13 | 36 | 11 | 37 | 9 | 6 | 15 | 35 | 14 | 49 | 20 | 61 | 30 | 0 | 6 | 29 | 16 | 4 | 17 | 8 | 17 | 56 | 14 | 59 | 20 | 66 | 18 | 6 | 5 | 66 | 24 | -11 | 8 |
| 32PmC9 | 3 | 7 | 8 | 3 | 3 | 14 | 8 | 6 | 6 | 9 | 6 | 6 | 6 | 3 | 6 | 1 | 5 | 8 | 4 | 4 | 11 | 0 | 7 | 4 | 11 | 5 | 2 | 13 | 8 | 0 | 0 | 13 | 0 | 0 | 0 | 5 |
| 35PmC15 | 70 | 21 | 55 | 15 | 79 | 15 | 44 | 24 | 68 | 24 | 42 | 24 | 60 | 7 | 58 | 17 | 6 | 10 | 2 | 7 | 5 | 12 | 69 | 9 | 63 | 1 | 36 | 20 | 74 | 14 | 5 | 11 | 36 | 28 | 0 | 5 |
| 49APmC84 | -3 | 3 | 5 | 11 | 2 | 11 | 4 | 6 | 9 | 3 | 4 | 7 | 1 | 1 | 4 | 11 | -1 | 8 | -5 | 12 | -13 | 2 | 7 | 0 | 1 | 5 | 3 | 7 | -1 | 4 | -1 | 9 | 0 | 1 | -8 | 8 |
| 56Pm942 | 52 | 14 | 59 | 21 | 51 | 27 | -11 | 3 | 44 | 14 | 10 | 3 | -18 | 4 | 47 | 4 | 3 | 6 | 13 | 5 | -6 | 16 | 61 | 14 | 35 | 20 | 54 | 18 | 79 | 13 | 57 | 9 | 0 | 3 | -3 | 0 |
| 56APm942 | -5 | 2 | -2 | 4 | -1 | 1 | -1 | 3 | 0 | 6 | 0 | 5 | 2 | 2 | 3 | 9 | -1 | 8 | -2 | 9 | -6 | 5 | -9 | 9 | -9 | 4 | -5 | 5 | -12 | 5 | -9 | 9 | -1 | 3 | -1 | 7 |
| 62Pm1984 | 4 | 1 | -4 | 4 | 6 | 4 | 2 | 2 | 7 | 5 | 5 | 6 | 4 | 7 | 3 | 4 | 6 | 12 | 2 | 5 | -1 | 4 | -11 | 2 | -4 | 4 | 4 | 2 | -3 | 5 | 15 | 10 | 0 | 9 | -9 | 7 |
| 66APm2867 | 35 | 25 | 46 | 15 | 39 | 21 | 15 | 19 | 49 | 6 | 23 | 20 | 38 | 3 | 73 | 7 | 5 | 4 | 9 | 9 | 0 | 4 | 11 | 10 | 10 | 3 | 12 | 9 | 28 | 23 | 43 | 22 | 20 | 10 | 6 | 5 |
| 71Pm4955 | -2 | 4 | -9 | 10 | -3 | 4 | -2 | 0 | -4 | 4 | 1 | 2 | 2 | 3 | 6 | 3 | -1 | 2 | -3 | 3 | -2 | 13 | 3 | 8 | -3 | 5 | -4 | 5 | 2 | 1 | 1 | 3 | -3 | 3 | 1 | 5 |
| 71APm4955 | -5 | 1 | -1 | 11 | -2 | 2 | 1 | 3 | -2 | 3 | 2 | 2 | 3 | 3 | 3 | 1 | -7 | 4 | -14 | 77 | 2 | 6 | 0 | 2 | 5 | 1 | 0 | 5 | 1 | 7 | -6 | 17 | -15 | 19 | -2 | 1 |
| 75Pm1090 | -8 | 18 | 2 | 16 | -5 | 10 | 4 | 10 | 6 | 0 | -4 | 4 | -1 | 4 | 3 | 9 | -3 | 9 | -5 | 3 | 3 | 7 | 2 | 6 | 7 | 8 | -5 | 7 | 3 | 16 | -9 | 10 | -10 | 8 | -4 | 7 |

| PHAGES | 2337 | | 2733 | | 2833 | | 2867 | | 3059 | | 3907 | | 4107 | | 4490 | | 4956 | | 5211 | | 5932 | | 6042 | | 1090 | | 5628 | | 8709 | | THE NUMBER OF STRAINS, WHICH BIOFILM WAS DESTROYED | |
|---|---|---|---|---|---|---|---|---|---|---|---|---|---|---|---|---|---|---|---|---|---|---|---|---|---|---|---|---|---|---|---|
| | | | | | | | | | | | | | P. MIRABILIS STRAINS | | | | | | | | | | | | | | | | | | | |
| | | | | | | | | | | | | | % OF BIOFILM DESTRUCTION | | | | | | | | | | | | | | | | | | | |
| | Z | SD | Z | SD | Z | SD | Z | SD | Z | SD | Z | SD | Z | SD | Z | SD | Z | SD | Z | SD | Z | SD | Z | SD | Z | SD | Z | SD | Z | SD | >50% | >75% |
| 39APmC32 | 97 | 2 | 29 | 19 | 67 | 13 | 67 | 15 | 47 | 9 | 71 | 20 | 96 | 4 | 95 | 3 | 76 | 16 | 56 | 12 | 95 | 7 | 89 | 10 | 92 | 6 | 42 | 19 | 61 | 2 | 31 | 11 |
| 65APm2833 | 86 | 5 | 84 | 5 | 64 | 22 | 52 | 18 | 45 | 4 | 68 | 15 | 89 | 7 | 77 | 6 | 53 | 17 | 65 | 15 | 86 | 3 | 81 | 3 | 49 | 18 | 16 | 17 | 54 | 28 | 18 | 6 |
| 72APm5211 | 98 | 1 | 77 | 8 | 85 | 5 | 80 | 16 | 62 | 7 | 87 | 2 | 93 | 4 | 96 | 3 | 88 | 3 | 82 | 5 | 96 | 3 | 80 | 3 | 92 | 4 | 45 | 20 | 90 | 3 | 26 | 15 |
| 32PmC9 | 3 | 10 | -7 | 11 | 2 | 1 | 7 | 8 | 14 | 5 | 11 | 5 | 5 | 7 | 2 | 1 | 11 | 9 | 3 | 3 | 5 | 6 | 4 | 6 | 1 | 3 | 10 | 0 | 1 | 6 | 0 | 0 |
| 35PmC15 | 97 | 2 | 81 | 17 | 59 | 20 | 78 | 18 | 50 | 14 | 81 | 10 | 95 | 3 | 94 | 2 | 71 | 22 | 65 | 7 | 94 | 4 | 69 | 8 | 94 | 2 | 56 | 13 | 86 | 8 | 33 | 11 |
| 49APmC84 | 1 | 2 | -5 | 8 | -4 | 6 | 0 | 5 | 35 | 35 | 16 | 10 | 6 | 1 | -1 | 8 | 12 | 4 | 11 | 2 | 1 | 1 | 4 | 8 | 2 | 2 | 4 | 0 | -4 | 13 | 0 | 0 |
| 56Pm942 | 58 | 8 | 75 | 7 | 71 | 19 | 75 | 12 | 51 | 18 | 73 | 14 | 90 | 3 | 78 | 12 | 67 | 7 | 55 | 20 | 92 | 4 | 66 | 3 | 51 | 18 | 7 | 3 | 61 | 21 | 25 | 8 |
| 56APm942 | 31 | 4 | -4 | 1 | 5 | 16 | -3 | 4 | 0 | 0 | -4 | 7 | 24 | 0 | -14 | 0 | 9 | 7 | -10 | 7 | 25 | 24 | -1 | 1 | 15 | 14 | 2 | 3 | 16 | 22 | 3 | 1 |
| 62Pm1984 | 78 | 18 | 64 | 22 | 57 | 20 | 81 | 15 | 41 | 27 | 21 | 2 | 68 | 1 | 42 | 8 | 58 | 23 | 64 | 23 | 77 | 14 | 56 | 17 | 76 | 10 | 61 | 15 | 67 | 14 | 15 | 4 |
| 66APm2867 | 74 | 12 | -1 | 4 | 24 | 20 | 37 | 18 | 9 | 8 | 62 | 20 | 90 | 9 | 75 | 19 | 39 | 21 | 8 | 12 | 3 | 3 | 3 | 17 | 37 | 3 | 40 | 26 | 21 | 21 | 9 | 3 |
| 71Pm4955 | 9 | 4 | -8 | 7 | 0 | 5 | 3 | 6 | 8 | 2 | 10 | 16 | 17 | 15 | 12 | 14 | 6 | 6 | 6 | 6 | 3 | 11 | -7 | 5 | 5 | 5 | -4 | 3 | -3 | 11 | 1 | 1 |
| 71APm4955 | 78 | 8 | -13 | 11 | 5 | 6 | 9 | 18 | 0 | 2 | 0 | 2 | 75 | 20 | 5 | 11 | -8 | 16 | 16 | 16 | 67 | 18 | 8 | 0 | 72 | 3 | -9 | 7 | 41 | 11 | 9 | 3 |
| 75Pm1090 | 80 | 16 | 9 | 2 | -9 | 2 | -2 | 4 | 30 | 21 | 2 | 5 | 49 | 6 | -5 | 3 | 14 | 3 | 8 | 2 | 83 | 19 | 8 | 7 | 69 | 2 | 16 | 21 | 2 | 4 | 5 | 3 |

| PHAGES | C5 X | C5 SD | C6 X | C6 SD | C7 X | C7 SD | C8 X | C8 SD | C9 X | C9 SD | C11 X | C11 SD | C12 X | C12 SD | C15 X | C15 SD | C20 X | C20 SD | C24 X | C24 SD | C31 X | C31 SD | C32 X | C32 SD | C33 X | C33 SD | C34 X | C34 SD | C41 X | C41 SD | C44 X | C44 SD | C46 X | C46 SD | C57 X | C57 SD |
|---|---|---|---|---|---|---|---|---|---|---|---|---|---|---|---|---|---|---|---|---|---|---|---|---|---|---|---|---|---|---|---|---|---|---|---|---|
| 39APmC32 | 80 | 1 | 86 | 5 | 87 | 5 | 68 | 14 | 85 | 5 | 78 | 7 | 77 | 17 | 76 | 12 | -2 | 12 | 83 | 4 | 87 | 5 | 85 | 7 | 74 | 5 | 87 | 10 | 91 | 8 | 82 | 10 | 94 | 3 | 56 | 14 |
| 65APm2833 | 81 | 7 | 66 | 8 | 71 | 7 | 52 | 14 | 69 | 12 | 81 | 11 | 81 | 10 | 81 | 10 | 0 | 4 | 82 | 4 | 70 | 13 | 44 | 12 | 70 | 11 | 58 | 14 | 52 | 2 | 55 | 10 | -4 | 4 | 82 | 3 |
| 72APm5211 | 87 | 4 | 45 | 14 | 47 | 16 | 75 | 13 | 17 | 13 | 82 | 7 | 81 | 12 | 69 | 4 | -1 | 7 | 89 | 4 | 87 | 5 | 87 | 6 | 72 | 7 | 87 | 8 | 96 | 5 | 28 | 8 | 90 | 5 | 47 | 16 |
| 32PmC9 | 2 | 7 | 4 | 4 | 2 | 3 | 7 | 7 | 48 | 12 | 13 | 7 | 21 | 29 | 8 | 7 | 72 | 8 | 0 | 4 | 79 | 18 | 55 | 20 | 44 | 11 | 42 | 19 | 43 | 14 | 24 | 6 | 3 | 3 | 28 | 20 |
| 35PmC15 | 79 | 3 | 85 | 2 | 74 | 8 | 52 | 5 | 90 | 2 | 84 | 8 | 86 | 6 | 89 | 4 | 58 | 4 | 88 | 6 | 86 | 7 | 79 | 8 | 65 | 10 | 92 | 8 | 96 | 6 | 65 | 11 | 49 | 24 | 76 | 17 |
| 49APmC84 | 7 | 4 | 1 | 3 | 0 | 4 | 1 | 9 | 32 | 11 | 11 | 7 | 0 | 8 | 2 | 6 | 41 | 6 | 0 | 4 | 82 | 7 | 36 | 3 | 41 | 5 | 25 | 9 | 31 | 5 | 23 | 5 | 92 | 7 | 1 | 12 |
| 56Pm942 | 84 | 8 | 65 | 15 | 70 | 12 | 78 | 14 | 57 | 10 | 81 | 8 | 82 | 7 | 84 | 5 | 1 | 4 | 71 | 6 | 62 | 19 | 41 | 8 | 69 | 8 | 62 | 13 | 50 | 11 | 57 | 11 | 62 | 9 | 86 | 6 |
| 56APm942 | 6 | 7 | 0 | 3 | -1 | 3 | -1 | 11 | 0 | 1 | 2 | 10 | 0 | 8 | 5 | 9 | -4 | 7 | 1 | 5 | 1 | 4 | -1 | 3 | 0 | 4 | 2 | 2 | 7 | 0 | -3 | 4 | -5 | 2 | -6 | 17 |
| 62Pm1984 | 2 | 18 | -3 | 4 | -3 | 4 | -5 | 4 | -3 | 5 | -4 | 12 | 4 | 7 | -9 | 6 | -2 | 2 | 16 | 12 | 3 | 2 | 34 | 13 | -2 | 13 | 29 | 8 | 48 | 8 | -2 | 4 | 23 | 8 | 14 | 24 |
| 66APm2867 | 81 | 9 | 67 | 9 | 72 | 10 | 80 | 7 | 70 | 4 | 79 | 10 | 74 | 14 | 88 | 7 | 0 | 8 | 80 | 11 | 75 | 11 | 81 | 8 | 76 | 1 | 79 | 11 | 58 | 13 | 56 | 6 | 45 | 9 | 75 | 9 |
| 71Pm4955 | 4 | 2 | 0 | 5 | -1 | 2 | -2 | 11 | 2 | 4 | 6 | 6 | -1 | 7 | 2 | 4 | 1 | 4 | 2 | 4 | 3 | 5 | 3 | 3 | -1 | 7 | 2 | 2 | -3 | 3 | -3 | 5 | 60 | 27 | 7 | 9 |
| 71APm4955 | 34 | 19 | -1 | 3 | 0 | 4 | 28 | 23 | 1 | 5 | 39 | 24 | 25 | 14 | 31 | 23 | 1 | 8 | 26 | 12 | 84 | 5 | 1 | 5 | 7 | 2 | 34 | 15 | 53 | 21 | 0 | 6 | 15 | 22 | 5 | 8 |
| 75Pm1090 | 69 | 9 | 1 | 5 | 0 | 4 | 33 | 37 | 2 | 4 | 39 | 39 | 31 | 32 | 41 | 37 | 9 | 7 | 32 | 39 | 84 | 4 | 7 | 7 | 3 | 7 | 3 | 7 | 8 | 15 | 0 | 6 | -4 | 5 | 62 | 9 |

% OF PLANKTONIC FORMS GROWTH REDUCTION
P. MIRABILIS STRAINS

% OF PLANKTONIC FORMS GROWTH REDUCTION

P. MIRABILIS STRAINS

| PHAGES | C70 | | C71 | | C77 | | C84 | | MM | | 332 | | 484 | | 512 | | 677 | | 687 | | 942 | | 977 | | 1220 | | 1281 | | 1579 | | 1683 | | 1984 | |
|---|---|---|---|---|---|---|---|---|---|---|---|---|---|---|---|---|---|---|---|---|---|---|---|---|---|---|---|---|---|---|---|---|---|---|
| | x̄ | SD | x̄ | SD | x̄ | SD | x̄ | SD | x̄ | SD | x̄ | SD | x̄ | SD | x̄ | SD | x̄ | SD | x̄ | SD | x̄ | SD | x̄ | SD | x̄ | SD | x̄ | SD | x̄ | SD | x̄ | SD | x̄ | SD |
| 39APmC32 | 91 | 8 | 58 | 3 | 38 | 14 | 87 | 7 | 90 | 8 | 97 | 5 | 98 | 2 | 92 | 6 | 99 | 0 | 99 | 1 | 93 | 5 | 4 | 4 | -3 | 4 | 94 | 3 | -8 | 5 | 96 | 3 | 97 | 3 |
| 65APm2833 | 66 | 17 | 56 | 8 | 39 | 18 | 80 | 6 | 77 | 5 | 93 | 3 | 83 | 10 | 62 | 16 | 98 | 1 | 75 | 28 | 84 | 6 | 0 | 3 | -2 | 5 | 95 | 5 | 1 | 1 | 49 | 11 | 54 | 16 |
| 72APm5211 | 91 | 3 | 24 | 7 | 28 | 18 | 86 | 7 | 84 | 5 | 97 | 3 | 95 | 3 | 95 | 5 | 99 | 0 | 97 | 3 | 75 | 22 | 72 | 2 | -1 | 2 | 95 | 4 | -2 | 2 | 79 | 13 | 96 | 4 |
| 32PmC9 | 63 | 15 | 26 | 10 | 45 | 5 | 74 | 15 | 38 | 3 | 31 | 5 | 75 | 14 | 34 | 8 | 30 | 6 | 39 | 4 | 51 | 28 | -2 | 2 | 5 | 4 | 45 | 4 | 3 | 3 | 12 | 5 | 32 | 4 |
| 35PmC15 | 94 | 5 | 59 | 4 | 33 | 19 | 94 | 7 | 96 | 3 | 92 | 8 | 98 | 2 | 89 | 8 | 100 | 0 | 95 | 5 | 89 | 14 | 0 | 3 | -5 | 2 | 94 | 7 | -1 | 2 | 90 | 7 | 99 | 2 |
| 49APmC84 | 32 | 6 | 24 | 7 | -1 | 6 | 63 | 11 | 33 | 10 | 30 | 4 | 81 | 8 | 68 | 8 | 79 | 13 | 51 | 13 | 76 | 13 | 1 | 3 | 3 | 5 | 58 | 5 | -2 | 3 | 37 | 13 | 34 | 3 |
| 56Pm942 | 63 | 22 | 60 | 7 | 36 | 15 | 81 | 5 | 75 | 12 | 68 | 21 | 83 | 14 | 68 | 21 | 96 | 2 | 90 | 15 | 69 | 27 | -1 | 2 | 3 | 3 | 92 | 3 | -2 | 3 | 51 | 5 | 47 | 2 |
| 56APm942 | -2 | 6 | -1 | 4 | -1 | 10 | 0 | 6 | -1 | 1 | 34 | 8 | 32 | 12 | 34 | 4 | 58 | 7 | 56 | 12 | 40 | 4 | -1 | 2 | -2 | 3 | 58 | 4 | -1 | 3 | 9 | 5 | 42 | 8 |
| 62Pm1984 | 66 | 10 | -3 | 3 | -4 | 3 | 48 | 9 | 47 | 11 | 44 | 2 | 51 | 13 | 34 | 8 | 65 | 6 | 58 | 21 | 35 | 1 | 2 | 1 | 0 | 4 | 67 | 6 | -3 | 3 | 2 | 11 | 58 | 8 |
| 66APm2667 | 72 | 16 | 66 | 11 | 59 | 14 | 84 | 9 | 83 | 9 | 95 | 2 | 93 | 7 | 83 | 12 | 93 | 7 | 95 | 3 | 86 | 10 | -2 | 2 | -3 | 4 | 93 | 4 | -1 | 2 | 78 | 12 | 57 | 11 |
| 71APm4955 | 35 | 12 | -1 | 2 | -5 | 10 | 4 | 2 | -1 | 1 | 16 | 6 | 39 | 10 | 3 | 4 | 19 | 4 | -1 | 3 | -1 | 1 | 1 | 1 | 3 | 3 | 11 | 6 | 2 | 2 | -7 | 3 | 8 | 6 |
| 71APm4955 | 82 | 10 | 3 | 4 | 0 | 9 | 44 | 19 | -4 | 6 | 58 | 7 | 61 | 6 | 36 | 8 | 70 | 8 | 65 | 5 | 43 | 10 | 75 | 10 | 2 | 2 | 65 | 6 | -3 | 2 | 83 | 11 | 34 | 14 |
| 75Pm1090 | 59 | 13 | 4 | 2 | 3 | 13 | 73 | 3 | 0 | 6 | 57 | 7 | 58 | 13 | 29 | 11 | 66 | 8 | 43 | 32 | 37 | 6 | 69 | 17 | 2 | 7 | 64 | 7 | 0 | 5 | 66 | 10 | 28 | 7 |

FIG. 10 Cont. 2

| CONT. | | P. MIRABILIS STRAINS | | | | | | | | | | | | | | | | | | | | | | | | | | | | | | | THE NUMBER OF STRAINS, WHICH PLANKTONIC FORMS GROWTH WAS REDUCED | |
|---|---|---|---|---|---|---|---|---|---|---|---|---|---|---|---|---|---|---|---|---|---|---|---|---|---|---|---|---|---|---|---|---|---|---|
| | | 2337 | | 2733 | | 2833 | | 2867 | | 3059 | | 3907 | | 4107 | | 4490 | | 4955 | | 5211 | | 5932 | | 6042 | | 1090 | | 5628 | | 8709 | | | |
| PHAGES | | % of planktonic forms growth reduction | | | | | | | | | | | | | | | | | | | | | | | | | | | | | | >80% | >95% |
| | | x̄ | SD | x̄ | SD | x̄ | SD | x̄ | SD | x̄ | SD | x̄ | SD | x̄ | SD | x̄ | SD | x̄ | SD | x̄ | SD | x̄ | SD | x̄ | SD | x̄ | SD | x̄ | SD | x̄ | SD | | |
| 39APmC32 | | 99 | 2 | 93 | 6 | 97 | 3 | 97 | 3 | 90 | 3 | 94 | 7 | 99 | 0 | 98 | 2 | 95 | 4 | 97 | 3 | 97 | 3 | 97 | 4 | 96 | 2 | 97 | 3 | 98 | 2 | 36 | 18 |
| 65APm2833 | | 47 | 10 | 47 | 7 | 42 | 4 | 98 | 1 | 60 | 1 | 83 | 18 | 97 | 4 | 59 | 23 | 45 | 11 | 61 | 22 | 96 | 6 | 64 | 19 | 98 | 1 | 78 | 15 | 98 | 3 | 18 | 6 |
| 72APm5211 | | 96 | 4 | 95 | 6 | 87 | 12 | 95 | 3 | 85 | 3 | 95 | 10 | 96 | 4 | 92 | 7 | 96 | 4 | 92 | 5 | 96 | 5 | 89 | 8 | 91 | 4 | 96 | 3 | 82 | 4 | 35 | 17 |
| 32PmC9 | | 30 | 3 | 32 | 5 | 14 | 9 | 31 | 4 | 32 | 4 | 39 | 13 | 27 | 8 | 34 | 2 | 30 | 5 | 20 | 9 | 30 | 5 | 47 | 7 | 48 | 20 | 53 | 13 | 52 | 12 | 0 | 0 |
| 35PmC15 | | 99 | 1 | 95 | 6 | 95 | 6 | 95 | 6 | 87 | 6 | 94 | 4 | 100 | 1 | 95 | 6 | 97 | 3 | 96 | 4 | 99 | 5 | 94 | 6 | 95 | 5 | 98 | 2 | 100 | 1 | 37 | 15 |
| 49APmC84 | | 32 | 5 | 61 | 21 | 15 | 5 | 34 | 2 | 64 | 2 | 52 | 26 | 51 | 8 | 38 | 4 | 31 | 3 | 26 | 4 | 37 | 14 | 51 | 9 | 76 | 11 | 58 | 15 | 57 | 17 | 2 | 0 |
| 56Pm942 | | 73 | 19 | 51 | 13 | 90 | 5 | 62 | 2 | 58 | 23 | 45 | 13 | 97 | 1 | 81 | 21 | 43 | 8 | 75 | 24 | 98 | 1 | 59 | 22 | 79 | 27 | 79 | 14 | 65 | 22 | 15 | 3 |
| 56APm942 | | 58 | 6 | 62 | 10 | 61 | 8 | 54 | 3 | 62 | 13 | 46 | 18 | 74 | 6 | 55 | 2 | 63 | 12 | 62 | 4 | 32 | 12 | 44 | 3 | 61 | 6 | 44 | 8 | 60 | 4 | 0 | 0 |
| 62Pm1984 | | 66 | 5 | 61 | 9 | 62 | 8 | 55 | 6 | 44 | 17 | 64 | 22 | 62 | 4 | 66 | 3 | 63 | 4 | 64 | 4 | 40 | 5 | 70 | 4 | 74 | 8 | 61 | 11 | 78 | 13 | 0 | 0 |
| 66APm2867 | | 94 | 10 | 75 | 18 | 92 | 12 | 92 | 8 | 88 | 7 | 85 | 12 | 94 | 10 | 87 | 9 | 86 | 18 | 90 | 10 | 97 | 1 | 83 | 15 | 90 | 18 | 98 | 1 | 87 | 16 | 26 | 4 |
| 71Pm4955 | | 41 | 15 | 11 | 6 | 15 | 7 | 12 | 7 | 3 | 9 | 15 | 1 | 36 | 10 | 13 | 5 | 21 | 4 | 20 | 3 | 31 | 12 | 17 | 3 | 62 | 18 | 20 | 5 | 6 | 7 | 0 | 0 |
| 71APm4955 | | 68 | 4 | 65 | 5 | 58 | 14 | 53 | 9 | 38 | 15 | 61 | 10 | 70 | 6 | 65 | 14 | 61 | 8 | 62 | 8 | 69 | 6 | 56 | 11 | 91 | 4 | 55 | 14 | 58 | 12 | 4 | 0 |
| 75Pm1090 | | 65 | 2 | 65 | 5 | 55 | 14 | 48 | 8 | 26 | 7 | 52 | 7 | 69 | 5 | 57 | 4 | 56 | 3 | 57 | 8 | 64 | 7 | 50 | 8 | 88 | 3 | 36 | 7 | 52 | 15 | 3 | 0 |

BACTERIOPHAGE STRAINS AGAINST PROTEUS MIRABILIS AND USE THEREOF

The invention relates to new bacteriophage strains deposited on Jun. 19, 2015 with the Polish Collection of Microorganisms (PCM) at Instytut Immunologii i Terapii Doświadczalnej Polskiej Akademii Nauk (The Immunology and Experimental Therapy Institute of the Polish Academy of Science), in Wroclaw, P L (Rudolfa Weigla 1, 53-114 Wroclaw) in accordance with the provisions of the Budapest Treaty on the International Recognition of the Deposit of Microorganisms for the Purposes of Patent Procedure, under the access numbers F/00084, F/00085 and F/00086, as well as to their medical use. In the further part of the present documentation the bacteriophage strains according to the present invention may be identified also by alternative names i.e. 72APm5211 (F/00084), 39APmC32 (F/00085) and 65APm2833 (F/00086).

Bacteriophages are viruses possessing a natural ability to destroy bacteria and commonly occurring in the environment as well as human and animal intestinal tracts [Ackermann H. W.: Bacteriophage taxonomy. Microbiol. Australia, 2011; 2: 90-94]. Nowadays, due to the availability of advanced research methods, bacteriophages have become a tool in the fight against multidrug-resistant microorganisms or undesirable bacteria in the industry as well as a tool used in diagnostics and molecular biology. The fight against bacteria involves using virulent phages, which, as a result of the process of propagation in bacteria, lead to their destruction, and release of progeny viruses capable of infecting other bacterial cells [Maura D., Debarbieux L.: Bacteriophages as twenty-first century antibacterial tools for food and medicine. Apel. Microbiol. Biotechnol., 2011; 90: 851-859].

The main advantage of phages is their high specificity towards bacteria, which is connected with the existence of specific receptors on the host cells. In consequence, bacteria belonging to a certain species or even strain are destroyed without affecting the patient's natural microflora. Enzymes produced by phages responsible for the degradation of the bacterial cell wall or capsule arouse interest as potential therapeutic agents or components of disinfectants. These enzymes belong to a novel group of drugs called enzybiotics [Drulis-Kawa Z., Majkowska-Skrobek G., Maciejewska B., Delattre A. S. and Lavigne R.: Learning from bacteriophages—advantages and limitations of phage and phage-encoded protein applications. Curr. Protein Pept. Sci, 2012; 13: 699-722].

Contemporary studies focus on lysins, which cause lysis of bacteria and release of descendant viruses, and depolymerases, which degrade capsular polysaccharides or exopolysaccharides (EPS), which are the main components of the bacterial biofilm matrix. Lysins are potential antibacterial agents acting mainly against Gram-positive bacteria [Borysowski J., Łobocka M., Międzybrodzki R., Weber-Dąbrowska B., Górski A.: Potential of bacteriophages and their lysins in the treatment of MRSA. Current status and future perspectives. Biodrugs, 2011; 25: 347-355]. In the case of Gram-negative bacteria their outer membrane protects peptydoglycan against the activity of lysins. Polysaccharide depolymerases have been examined in terms of their applicability for fighting infections connected with biofilm formation or caused by capsule producing bacteria responsible, among others, for meningitis, pneumonia, bone marrow inflammation, septicemia, septic arthritis or pyelonephritis. To date polysaccharide depolymerases have been detected in various phages infecting e.g. *E. coli*, [Bessler W., Fehmel F., Freund-Mölbert E., Knüfermann H., Strim S.: *Escherichia coli* capsule bacteriophages IV. Free capsule depolymerase 29. J. Virol., 1975; 15: 976-984; Clarke B. R., Esumeh F., Roberts I. S.: Cloning, expression, and purification of the K5 capsular polysaccharide lyase (KflA) from coliphage K5A: evidence for two distinct K5 lyase enzymes. J. Bacteriol., 2000; 182: 3761-3766], *P. aeruginosa* [Bartell P. F., Orr T. E., Lam G. K. L.: Purification and properties of polysaccharide depolymerase associated with phage-infected *Pseudomonas aeruginosa*. J. Biol. Chem., 1968; 243: 2077-2080; Glonti T., Chanishvili N., Taylor P. W.: Bacteriophage-derived enzyme that depolymerizes the alginic acid capsule associated with cystic fibrosis isolates of *Pseudomonas aeruginosa*. J. Appl. Microbiol., 2010; 108: 695-702], *Klebsiella* [Hsu Ch. R., Lin T. L., Pan Y. J., Hsieh P. F., Wang J. T.: Isolation of a bacteriophage specific for a new capsular type of *Klebsiella pneumoniae* and characterization of its polysaccharide depolymerase. PLOS ONE, 2013; 8: e70092; Yang L., Li G., Mo Z., Chai Z., Shang A., Mou H.: Properties of *Klebsiella* phage P13 and associated exopolysaccharide depolymerase. J. Ocean Univ. China, 2014; 13: 163-168], *Streptococcus* [Lindsay A.-M., Zhang M., Mitchell Z., Holden M. T. G., Waller A. S., Sutcliffe I. C., Black G. W.: The *Streptococcus equi* prophage-encoded protein SEQ2045 is a hyaluronan-specific hyaluronate lyase that is produced during equine infection. Microbiology, 2009; 155: 443-449; El-Saforya N. S., Leeb G. C., Leea C. K.: Characterization of hyaluronate lyase from *Streptococcus pyogenes* bacteriophage H4489A. Carbohydrate Polymers, 2011; 84: 1182-1191], *Erwinia amylovara* [Vandenbergh P. A., Wright A. M. and Vidaver A. K.: Partial purification and characterization of a polysaccharide depolymerase associated with phage-infected *Erwinia amylovora*. Appl. Environ. Microbiol., 1985; 49: 994-996] or *Vibrio cholerae* 0139 [Linnerborg M., Weintraub A., Albert M. J., Widwalm G.: Depolymerization of the capsular polysaccharide from *Vibrio cholerae* 0139 by a lyase associated with the bacteriophage JAL Carbohydrate Res., 2001; 333: 263-269]. At present there are no data available concerning polysaccharide depolymerases produced by phages specific to *Proteus mirabilis* (*P. mirabilis*).

It is known that phage polysaccharide depolymerases play an essential role in the destruction of the matrix of biofilm formed by other bacteria [Hughes K. A., Sutherland I. W., Jones M. V.: Biofilm susceptibility to bacteriophage attack: the role of phage-borne polysaccharide depolymerases. Microbiology, 1998; 144: 3039-3047; Gutierrez D., Martínez B., Rodríguez A. and Garcia P.: Genomic characterization of two *Staphylococcus epidermidis* bacteriophages with anti biofilm potential. BMC Genomics, 2012; 13: 228; Siringan P., Connerton P. L., Payne R. J. H., Connerton I. F.: Bacteriophage-mediated dispersal of *Campylobacter jejuni* biofilms. Appl. Environ. Microbiol., 2011; 77: 3320-3326]. It has been shown that these enzymes can cause a release of bacteria from the biofilm and, by destroying its matrix, they can enable various antimicrobial agents to gain access to the cells which it protects. Therefore, numerous studies are being conducted in order to develop effective combined methods for fighting bacterial biofilm. Attempts are being made to use bacteriophages and depolymerases produced by them in combination with antibiotics such as amoxicillin, ciprofloxacin or cefotaxime [Bedi M. S., Verma V., Chhibber S.: Amoxicillin and specific bacteriophage can be used together for eradication of biofilm of *Klebsiella pneumoniae* B5055. World J. Microbiol. Biotechnol., 2009; 25: 1145-1151; Verma V., Harjai K., Chhibber S.: Restricting ciprofloxacin induced resistant variant formation in biofilm of

*Klebsiella pneumoniae* B5055 by complementary bacteriophage treatment. J. Antimicrob. Chemiother., 2009; 64: 1212-1218; Ryan E. M., Alkawareek M. Y., Donnelly R. F. & Gilmore B. F.: Synergistic phage-antibiotic combinations for the control of *Escherichia coli* biofilms in vitro. FEMS Immunol. Med. Microbiol., 2012; 65: 395-398; Nouraldin A. A. M., Baddour M. M., Harfoush R. A. H., Essa S. A. A. M. Bacteriophage-antibiotic synergism to control planktonic and biofilm producing clinical isolates of *Pseudomonas aeruginosa*, Alex. J. Med., 2016; 52: 99-105], disinfectants Tait K., Skilmann L. C. and Sutherland I. W.: The efficacy of bacteriophage as a method of biofilm eradication. Biofouling, 2002; 18: 305-311; Zhang Y., Hu Z.: Combined treatment of *Pseudomonas aeruginosa* biofilms with bacteriophages and chlorine. Biotechnology and Bioengineering, 2013; 110: 286-295] or compounds chelating biogenic elements [Chhibber S., Nag D. and Bansal S.: Inhibiting biofilm formation by *Klebsiella pneumoniae* B5055 using an iron antagonizing molecule and a bacteriophage. BMC Microbiology, 2013; 13: 174]. The obtained results are very promising, however there is no data concerning the practical application of these methods for preventing *P. mirabilis* biofilm formation and its eradication.

*P. mirabilis* bacteria are Gram-negative opportunistic pathogens belonging to the family Enterobacteriaceae, which mainly cause of urinary tract infections (UTI), especially among catheterized patients or individuals with anatomical and/or physiological defects in the urinary tract or after surgeries [Jacobsen S. M., Shirtliff M. E.: *Proteus mirabilis* biofilms and catheter-associated urinary tract infections. Virulence, 2011; 2: 460-465]. It has been shown that in the case of catheterized hospital or ambulatory patients, the frequency of UTIs increases by 5% with each day of catheterization. It is connected with the formation of bacterial biofilm on the catheter surface, a structure resistant to the activity of disinfectants, antibiotics or host defense mechanisms [Moryl M., Torzewska A., Jałmużna P. and Różalski A.: Analysis of *Proteus mirabilis* distribution in multi-species biofilms on urinary catheters and determination of bacteria resistance to antimicrobial agents. Pol. J. Microbiol, 2013; 62: 377-384].

*P. mirabilis* is also associated with rheumatoid arthritis in humans, occurring as a UTI complication caused by these bacteria [Ebringer A, Rashid T.: Rheumatoid arthritis is an autoimmune disease triggered by *Proteus* urinary tract infection. Clin. Dev. Immunol. 2006; 13: 41-48]. A strong proteolytic activity of *P. mirabilis* also leads to meat spoilage [Bradeeba K., Sivakumaar P. K: Antibiotic susceptibility of selected pathogenic bacteria isolated from raw meat sample obtained from Chidambaram, Tamil Nadu. J. Chem. Pharm. Res., 2013, 5(1): 64-67].

Drugs currently recommended for the treatment of UTIs connected with the presence of a urinary catheter include fluorochinolones (ciprofloxacin), beta lactam antibiotics (amoxicillin with bacterial beta lactamase inhibitor—clavulanic acid, and others) $1^{st}$, $2^{nd}$ and $3^{rd}$ generation of cephalosporins and aminoglycosides (gentamicin, amikacin). In special cases it is recommended to use combined treatment.

Unfortunately, inappropriate use of antibiotics resulted in the selection of multidrug-resistant *P. mirabilis* strains [Kraśnicki K., Wolski Z., Mikucka A., Gospodarek E.: Wrażliwość pałeczek Gram-ujemnych na leki przeciwbakteryjne w oddziałach urologii. Przegląd Urologiczny, (Sensitivity of Gram-negative bacilli to antimicrobial drugs in urological wards. Urological Review), 2007/3 (43). Article in Polish; Schneider I., Markovska R., Marteva-Proevska Y., Mitov I., Markova B., Bauernfeind A.: Detection of CMY-99, a novel acquired AmpC-type β-lactamase, and VIM-1 in *Proteus mirabilis* isolates in Bulgaria. Antimicrob. Agents Chemother., 2014; 58: 620-621]. *P. mirabilis* bacilli resistance to β-lactam antibiotics is connected with the production of AmpC cephalosporinases, extended spectrum beta-lactamases ESBL and carbapenemase [Datta P., Gupta V., Arora S., Garg S., Chander J.: Epidemiology of extended-spectrum β-lactamase, AmpC, and carbapenemase production in *Proteus mirabilis*. Jpn. J. Infect. Dis. 2014; 67(1): 44-6]. There is an increasing number of reports on *P. mirabilis* resistance to broad-spectrum cephalosporins and ciprofloxacin [Sohn K. M., Kang C. I., Joo E. J., Ha Y. E., Chung D. R., Peck K. R., Lee N. Y., Song J. H.: Epidemiology of ciprofloxacin resistance and its relationship to extended-spectrum β-lactamase production in *Proteus mirabilis* bacteremia. Korean J. Intern. Med., 2011; 26(1): 89-93; Wang J. T., Chen P. C., Chang S. C., Shiau Y. R., Wang H. Y., Lai J. F., Huang I. W., Tan M. C., Lauderdale T. L.; TSAR Hospitals: Antimicrobial susceptibilities of *Proteus mirabilis*: a longitudinal nationwide study from the Taiwan surveillance of antimicrobial resistance (TSAR) program. BMC Infect. Dis. 2014; 14: 486].

Currently, in order to prevent infections connected with urinary bladder catheterization, the use of a catheter is recommended only in situations when it is absolutely necessary. Under these circumstances, while installing a catheter, the principles of the aseptic technique must be strictly obeyed, catheters must be regularly exchanged and a closed circuit drainage systems should be used with the urinary drainage bag placed below the bladder. An important role is also played by the material of which the catheter is made. The most commonly used materials are latex, polyurethane, silicone latex, silicone or vinyl polychloride. Silicone catheters are referred to as the gold standard due to their compatibility and the fact that they do not cause cytotoxic changes in the macroorganism tissues [Ostrowska K., Strzelczyk A., Różalski A., Stączek P.: Biofilm bakteryjny jako przyczyna zakażeń układu moczowego-mikroorganizmy patogenne, metody prewencji i eradykacji. Postępy Higieny i Medycyny Doświadczalnej (Bacterial biofilm as a cause of urinary tract infections—pathogens, methods of prevention and eradication. Advances in Hygiene and Experimental Medicine), 2013; 67: 1027-1033. Article in Polish]. Research is being conducted in order to create a material characterized by resistance to microbial adhesion and to develop technologies for coating catheters with substances limiting the bacterial adhesion or possessing bactericidal properties.

Due to numerous failures of the classic antibiotic therapy as well as equipment limitations, alternative methods of fighting *P. mirabilis* infections, especially those connected with biofilm formation, are being searched for. One of possible solutions is the use of specific bacteriophages.

To date little has been known about phages capable of infecting *P. mirabilis* bacteria or enzymes produced by them. Scientific publications from the 1970s and 1990s pointed to the differential potential of bacteriophages against the strains from the genus *Proteus* including *P. mirabilis* species [Hickman F. W., Farmer J. J. 3rd.: Differentiation of *Proteus mirabilis* by bacteriophage typing and the Dienes reaction. J. Clin. Microbiol., 1976; 3(3): 350-358; Schmidt W. C., Jeffries C. D.: Bacteriophage typing of *Proteus mirabilis, Proteus vulgaris*, and *Proteus morganii*. Appl. Microbiol., 1974; 27(1): 47-53; Sekaninová G., Rychlík I., Kolárová M., Pillich J., Seménka J., Zajícová V.: A new bacteriophage typing scheme for *Proteus mirabilis* and *Proteus vulgaris* strains. 3. Analysis of lytic properties. Folia Microbiol. (Praha). 1998; 43(2): 136-40].

Currently available publications indicate the possibility of using phages to fight biofilms formed by *P. mirabilis* bacteria [Carson L., Gorman S. P., Gilmore B. F.: The use of lytic bacteriophages in the prevention and eradication of biofilms of *Proteus mirabilis* and *Escherichia coli*. FEMS Immunol. Med. Microbiol., 2010; 1-9; Lehman S. M., Donlan R. M.: Bacteriophage-mediated control of a two-species biofilm formed by microorganisms causing catheter-associated urinary tract infections in an in vitro urinary catheter model. Antimicrob. Agents Chemother. 2015; 59(2): 1127-37; Nzakizwanayo J., Hanin A., Alves D. R., McCutcheon B., Dedi C., Salvage J., Knox K., Stewart B., Metcalfe A., Clark J., Gilmore B. F., Gahan C. G., Jenkins A. T., Jones B. V. Bacteriophage can prevent encrustation and blockage of urinary catheters by *Proteus mirabilis*. Antimicrob. Agents Chemother., 2015; 60(3): 1530-6; *Melo L. D. R., Veiga P., Cerca N., Kropinski A. M., Almeida C., Czeredo J., Sillankorva S.: Development of a phage cocktail to control Proteus mirabilis catheter-associated urinary tract infections. Front. Microbiol., 2016; 7: 1024*]. Literature data concerning other bacteria show that using single phages is not fully effective in combating biofilms. More promising results have been obtained by treating biofilms with a phage cocktail [Tait K., Skilmann L. C. and Sutherland I. W.: The efficacy of bacteriophage as a method of biofilm eradication. Biofouling, 2002; 18: 305-311; Fu W., Forster T., Mayer O., Curtin J. J., Lehman S. M., Donlan R. M.: Bacteriophage cocktail for the prevention of biofilm formation by *Pseudomonas aeruginosa* on catheters in an in vitro model system. Antimicrob. Agents Chemother., 2010; 54: 397-404; Alves D. R., Perez Esteban P., Kot W., Bean J. E., Arnot T., Hansen L. H., Enright M. C., Jenkins A. T. A.: A novel bacteriophage cocktail reduces and disperses *Pseudomonas aeruginosa* biofilms under static and flow conditions. Microbial Biotechnology, 2016; 9(1): 61-74].

In view of difficulties associated with prevention and treatment of urinary tract infections caused by *P. mirabilis*, in particular those linked with bladder catheterization and in view of high costs of treatment, it is the aim of the present invention to provide new bacteriophage strains for use in therapy and/or prophylaxis of diseases of bacterial etiology and in particular the strains virulent against bacteria of the species *Proteus mirabilis*, especially the drug- and multidrug-resistant strains of the species and/or able to destroy biofilm matrix of bacteria of the species *Proteus mirabilis*, especially the drug- and multidrug-resistant strains of the species. The aim of the present invention is also to provide bacteriophage products for use in medical and veterinary prophylaxis and therapy both alone and/or in combination with other anti-bacterial substances, in particular against bacteria of the species *Proteus mirabilis*, especially the drug- and multidrug-resistant strains of the species. A still further aim of the invention is to provide improved preparations and methods for use in industry, in particularly in the food industry, especially in meat industry, for control and prevention of colonization by bacteria of the species *Proteus mirabilis*, especially the drug- and multidrug-resistant strains of the species.

The present invention relates to the new bacteriophage strains specific against bacteria belonging to the species *P. mirabilis*, deposited with the Polish Collection of Microorganisms (PCM) under the access numbers: F/00084 (72APm5211), F/00085 (39APmC32), F/00086 (65APm2833), for use in therapy.

The present invention relates in particular to the new bacteriophage strains specific for bacteria belonging to the species *P. mirabilis*, deposited with the Polish Collection of Microorganisms (PCM) under the access numbers: F/00084 (72APm5211), F/00085 (39APmC32), F/00086 (65APm2833), in form of complete particles of the single bacteriophage strain, in form of bacteriophage lysates, optionally in form of purified bacteriophage proteins, in particular lytic enzymes that degrade the bacterial cell wall and enzymes that decompose bacterial extracellular polysaccharides, for use in therapy as anti-bacterial agents, in particular against bacteria of the species *Proteus mirabilis*, especially the drug- and multidrug-resistant strains of the species, advantageously in urinary tract infections.

The present invention relates in particular to the new bacteriophage strains specific against bacteria belonging to the species *P. mirabilis*, deposited with the Polish Collection of Microorganisms (PCM) under the access numbers: F/00084 (72APm5211), F/00085 (39APmC32), F/00086 (65APm2833), in form of a cocktail comprising two or more active bacteriophages, in form of lysates of two or more active bacteriophages, optionally in form of purified bacteriophage proteins of two or more active bacteriophages, especially lytic enzymes that degrade the bacterial cell wall and enzymes that decompose bacterial extracellular polysaccharides, for use in therapy as anti-bacterial agents, in particular against bacteria of the species *Proteus mirabilis*, especially the drug- and multidrug-resistant strains of the species, advantageously in urinary tract infections.

The invention covers also a use of at least one bacteriophage strain selected from the strains deposited with the Polish Collection of Microorganisms (PCM) under the access numbers: F/00084 (72APm5211), F/00085 (39APmC32), F/00086 (65APm2833), for manufacturing anti-bacterial preparations for combating bacteria belonging to the species *P. mirabilis*. The use of the bacteriophage strain relates to the use of complete bacteriophages in phage preparations consisting of a single phage strain, as well as the use of a cocktail comprising several or over a dozen active bacteriophages. The invention relates to the use of purified bacteriophage proteins, preferably the enzymes decomposing sugar and protein components of bacterial cell covers, preferably the bacterial cell wall and bacterial extracellular polysaccharides.

The bacteriophages of the invention are used in the form of a lysate, cocktail, purified bacteriophage proteins, in combination or in composition with other drugs and anti-bacterial agents, for the prophylaxis and treatment of infections caused by *P. mirabilis*, advantageously urinary tract infections.

The invention relates also to a use of the bacteriophages deposited under the PCM access numbers: F/00084 (72APm5211), F/00085 (39APmC32), F/00086 (65APm2833), in the form of a lysate, cocktail or composition with other anti-bacterial agents to disinfect meat products, as well as facilities and tools used in meat processing.

The invention relates also to a use of the bacteriophages of the invention deposited under the PCM access numbers: F/00084 (72APm5211), F/00085 (39APmC32), F/00086 (65APm2833), for the manufacturing a composition comprising stabilizers and other anti-bacterial components, meant for disinfection of surfaces and instruments of medical use and in food industry.

The bacteriophages, cocktails and compositions according to the invention are in liquid form intended for use in as spray, compresses, rinse/wash liquid preparation or wet compresses.

Alternatively, the bacteriophages, cocktails and compositions according to the invention are in gel form intended for coating medical devices, preferably urologic catheters.

The invention relates also to use of enzymes, preferably polysaccharide depolymerases of the bacteriophages deposited under the PCM access numbers: F/00084 (72APm5211), F/00085 (39APmC32), F/00086 (65APm2833), for the prophylaxis and treatment of infections caused by *P. mirabilis*.

The invention relates also to use of enzymes, preferably polysaccharide depolymerases of the bacteriophages deposited under the PCM access numbers: F/00084 (72APm5211), F/00085 (39APmC32), F/00086 (65APm2833) for manufacturing a composition comprising stabilizers and other anti-bacterial components, meant for disinfection of surfaces and instruments of medical use and in food industry, as well as meat and meat products.

The present invention enabled acquiring valuable preparations that can be used in the treatment and/or prophylaxis of diseases of bacterial etiology and in particular the preparations virulent against bacteria of the species *Proteus mirabilis*, especially drug- and multidrug-resistant strains of the species and/or able to destroy biofilm matrix of bacteria of the species *Proteus mirabilis*, especially the drug- and multidrug-resistant strains of the species. kill.

BRIEF DESCRIPTION OF THE DRAWINGS

The invention is described in detail below with reference to the drawings, wherein:

FIG. 7 presents Table 1.

FIG. 9 presents Table 3.

FIG. 10 presents Table 4.

DETAILED DESCRIPTION OF THE INVENTION

Definitions

Figure 1:
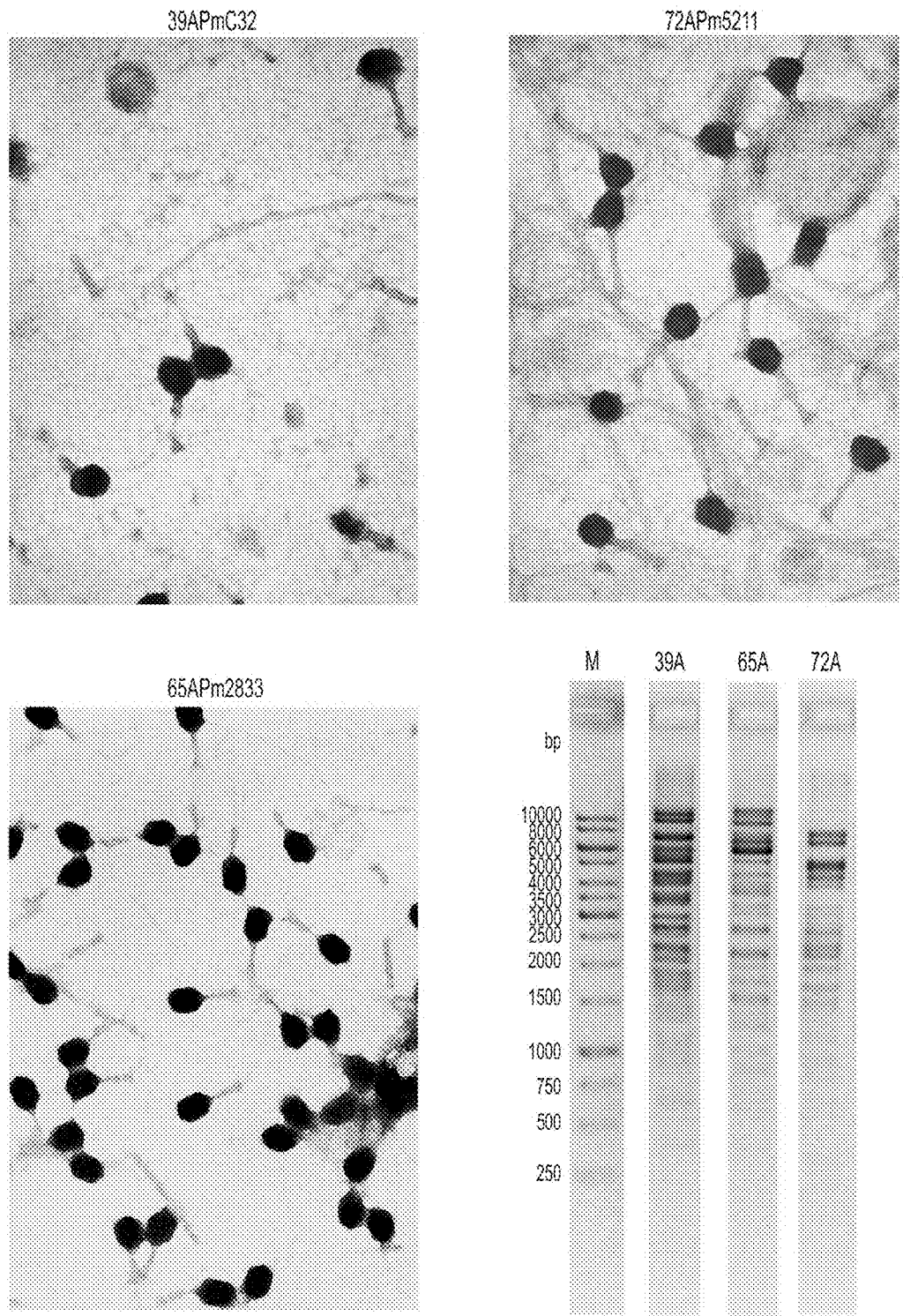
FIG. 1 shows the morphology of the bacteriophages of the present invention, obtained in the transmission electron microscope (magnification 60 000×) and their restriction profiles; 39APmC32=39A, 65A=65APm2833, 72A=72APm5211.

In the following description and claims, the terms used have the below defined meaning unless from the context of their use a different meaning evident.

The terms "bacteriophage" and "phage" are used interchangeably as synonyms.

The term "phage cocktail" refers to a mixture according to the invention comprising two or three bacteriophages deposited with The Polish Collection of Microorganisms (PCM) under the access numbers: F/00084 (72APm521), F/00085 (39APmC32), F/00086 (65APm2833). Phage cocktail may optionally also contain phages other than bacteriophages of the invention.

The term "biofilm eradication" or "biofilm destruction" or "inhibition of biofilm formation" is intended herein to mean the destruction of the biofilm or limitation of biofilm formation evaluated by testing the activity of bacterial cell dehydrogenases performed using the MTT assay.

The term "composition" herein means a prophylactically or therapeutically effective composition according to the invention comprising bacteriophages deposited under PCT access numbers: F/00085 (39APmC32), F/00086 (65APm2833), F/00084 (72APm5211), the bacteriophages being in form of whole particles of a single bacteriophage strain or in form of a phage cocktail, or in form of bacteriophage lysates, or optionally in form of purified bacteriophage proteins, especially lytic enzymes, that degrade the bacterial cell wall and enzymes that decompose bacterial extracellular polysaccharides.

The term "treatment" refers to both treatment and prophylaxis in human and in veterinary medicine, and the therapeutic effect is alleviation or reduction of the infection symptoms and improvement of the patient's condition, as well as preventing the infections and elimination of the effects of the same, up to complete eradication of infections.

As mentioned above, the problem of *P. mirabilis* infections is increasing due to the appearance of *P. mirabilis* multidrug resistant strains [Kraśnicki K., Wolski Z., Mikucka A., Gospodarek E.: Wrażliwość pałeczek Gram-ujemnych na leki przeciwbakteryjne w oddziałach urologii. Przegląd Urologiczny, (Sensitivity of Gram-negative bacilli to antimicrobial drugs in urological wards. Urological Review), 2007/3 (43). Article in Polish]. Furthermore, the characteristic feature of these uropathogens is an ability to form biofilm on urological catheters, which contributes to the development of urinary tract infection and complicates treatment. In the research which led to the solution according to the invention, 50 uropathogenic *P. mirabilis* strains were used. *P. mirabilis* strains came from the collection owned by the Department of Immunobiology of Bacteria, University of Lodz. 22 strains (C5, C6, C7, C8, C9, C11, C12, C15, C20, C24, C31, C32, C33, C34, C41, C44, C46, C57, C70, C71, C77, C84) were isolated from catheters obtained from patients of the Urological Outpatient Clinic, Pirogow's Hospital in Lodz, the remaining 28 strains (MM, 332, 484, 512, 677, 687, 942, 977, 1220, 1281, 1579, 1683, 1984, 2337, 2733, 2833, 2867, 3059, 3907, 4107, 4490, 4955, 5211, 5932, 6042, 1090, 5628, 8709) were isolated from the urine of patients with UTI treated in the Wards of Neurosurgery, Nephrology, Neurology Rehabilitation, The Children's Memorial Health Institute in Warsaw. The sensitivity of strains isolated from urological catheters biofilms to the 13 drugs had been determined earlier [Moryl M., Torzewska A., Jałmużna P. and Różalski A.: Analysis of *Proteus mirabilis* distribution in multi-species biofilms on urinary catheters and determination of bacteria resistance to antimicrobial agents. Pol. J. Microbiol, 2013; 62: 377-384]. Three strains were resistant to all tested drugs, whereas 91%, 86% and 82% of the isolates were resistant to gentamicin, cotrimoxazole and amoxycillin with clavulanic acid, respectively. 41% of the strains were insensitive to ciprofloxacin—a drug recommended in the first instance for the treatment of UTIs.

Bacteriophages were isolated from urban wastewater purified by centrifugation and filtration through a filter with a pore diameter of 0.2 μm. The purified wastewater samples were mixed at equal volumes with double concentrated TSB and next a fresh host culture was added. After 3 h incubation at 37° C. at 150 rpm/min. the culture was inoculated onto a phage nutrient agar plates [Ślopek S., Durlakowa I., Kucharewicz-Krukowska A., Krzywy T., Ślopek A., Weber B.: Phage typing of *Shigella flexneri*. Arch. Immunol. Therap. Exp., 1972; 20(1): 1-60]. If the host exhibited a swarming growth ability, the phage nutrient agar was supplemented with phenol (0.1%). After 24h incubation single plaques evidencing the presence of phages were cut out and transferred to nutrient broth pH 7.1, followed by the addition of the host culture. After the phages proliferation, the culture was centrifuged and filtered through filters with a pore diameter of 0.2 μm. The obtained lysates were diluted and a double agar layer method was performed to determine the titer and isolate single plaques. The procedure was repeated 5 times in order to obtain a pure line of phages. In this way 48 *P. mirabilis* specific phages were isolated from sewage. Phages 39APmC32, 65APm2833 and 72APm5211, according to the invention, formed respectively plaques with a diameter of 3 mm which were clear, surrounded by a 3 mm halo zone; plaques with a diameter of 1 mm which were clear; plaques with a 4 mm diameter surrounded by a 3 mm halo zone. Due to the planned use of the phages it was recommended that they should form plaques surrounded by a halo zone, which is formed as a result of the activity of phage enzymes degrading bacterial exopolysaccharides. It is a desirable phages property because polysaccharide depolymerases play an essential role in the degradation of bacterial capsules and the biofilm matrix, thus enabling the phages or other antibacterial agents to gain access to bacteria. According to the invention, advantageously bacteriophages 39APmC32 and 72APm5211 form plaques surrounded by large halo zones, which suggests that they produce polysaccharide depolymerases. The other phages also formed plaques surrounded by a halo zone, among which phages designated with the numbers 46, 49A, 56, 70 and 71A formed halo zones comparable to that produced by phages according to the invention. Based on the results obtained during the further studies, these phages were excluded from the invention.

An important property taken into account while selecting the phages according to the invention was the range of hosts sensitive to phage, advantageously phages should possess a broad range of hosts. In order to select such phages, the susceptibility of 50 uropathogenic *P. mirabilis* strains to the isolated phages was determined using the "spot-test" method. The group of bacteriophages possessing the broadest range of hosts included the phages: 28, 31, 34, 35, 37A, 38, 39A, 45, 65A, 66, 66A and 70. However, a complete or almost complete lysis of the bacterial lawn in at least 35 strains was caused by only 4 phages: 65A (44 strains), 66 (41 strains), 66A (35 strains) and 70 (44 strains). All the strains tested were sensitive to phages 35 and 45, however, a weak lysis of the lawn of the examined strains was observed. A complete or almost complete lysis was caused by these phages only in 30 and 27 strains, respectively. Advantageously, the bacteriophage 65A according to the invention completely lysed the bacterial lawn of as many as 39 *P. mirabilis* strains studied, with a simultaneous resistance of 2 isolates to this phage. Similarly, strongly lytic phages 66, 66A and 70 were not used in the presently disclosed invention, based on the results obtained in further research. According to the invention, for phages 39APmC32 and 72APm5211 positive lytic reactions (complete or almost complete lysis of bacteria from 26 and 24 strains, respectively) were observed on the level similar to that of the other 13 phages, including phages 46, 56 and 71A forming plaques with large halo zones. Unlike the other phages, viruses 39A and 72A produced plaques surrounded by a large halo zone. Bacteriophages which did not meet the requirement of possessing a broad range of hosts were not taken into consideration in spite of forming plaques surrounded by halo zones.

Due to the fact that all phages were isolated from the material collected a few times from the same sewage treatment plants and many of them were characterized by a similar range of hosts, their molecular analysis was performed. The analysis of DNA isolated from phages and treated with the experimentally selected enzyme EcoRV and subsequently separated in 1.2% agarose gel was done. The phages DNA was isolated using the method modified by Su et al. [Su M T, Tyamagondlu V. V., Bodmer R.: Large- and small-scale preparation of bacteriophage lambda lysate and DNA. BioTechniques, 1998; 25(1): 44-46]. The obtained restrictive profiles allowed constructing a dendrogram presenting the similarity within the isolated collection of phages. Additionally, three *P. vulgaris* specific phages 81Pv1595, 81APv1595 and 81BPv1595 were used. DNA of bacteriophage 58aPm1220 appeared to be insensitive to the enzyme EcoRV. The computer analysis of the restriction profiles of the 51 phages examined allowed classifying the viruses to 34 different types, designated with Roman figures, indicating at the same time that some of the phages in the collection were isolated a few times. Phages 39A, 65A and 72A (the full designation of which was presented above), which are the subject matter of the invention, were classified to the following types marked with the Roman figures: I, IV and VII. Type I includes also the phage 46PmC70, which, as mentioned before, formed plaques surrounded by large halo zones. The phages possessing the restriction profile I exhibited a 94.3% similarity to the phages presenting profile II (28PmC5, 31PmC8, 35PmC15, 38PmC31). Phage 66Pm2867, according to the invention with a lytic activity similar to phage 65A presented the same restriction profile IV. Moreover, the restriction profile IV was 97.1% identical to profile V presented by phage 70Pm4490. Type VII was presented only by phage 72A, however, it showed a 97.9% similarity to type VIII characteristic for phage 72B.

Bacteriophages 39APmC32, 65APm2833 and 72APm5211, deposited in PCM and marked with the above-mentioned numbers, which are the subject matter of the invention have been classified to the order Caudovirales, based on their morphology observed under an electron microscope. Moreover, phages 39APmC32 i 65APm2833 were found to possess a contractile tail, which suggests that they are members of the Myoviridae family. In the case of phage 72APm5211 only virions with noncontractile tails were detected and it probably represents the Siphoviridae family.

Bacteriophages 39APmC32, 65APm2833 and 72APm5211, which are the subject matter of the invention, have been characterized in terms of their susceptibility to physicochemical factors: temperature, pH and chloroform. Phages 65A and 72A maintained the level of their activity after 1h incubation at 37° C. in buffers with the pH range from 4 to 7, and phage 39A in the pH range from 5 to 7. The phages became inactivated after 1h incubation at 37° C. in the buffer with pH 2 and 12. The titers of phages 39A, 65A and 72A decreased to about 65%-70% after the incubation in PBS with pH 8. Comparing the activity of the phages incubated for 0.5 h and 1 h at different temperatures with the activity of the phages incubated at 37° C., it was revealed that viruses 65A and 72A maintained the same level of activity after the incubation at 50° C., and phage 39A exhibited activity reduced to 77% after 0.5 h and to 50% after 1 h of incubation. Incubation of phages at 60° C. for 0.5 h caused a decrease in their activity to about 55% and for 1 h to about 30-35% compared to the control. Phage 39A reduced its activity to 37% after the incubation at 60° C. for 0.5 h and to 12% after the incubation for 1 h. The studied phages lost their activity at the temperatures of 70 and 80° C. 50% chloroform caused a reduction in the titer of bacteriophages 39APmC32 and 65APm2833 to about 40%, and the titer of phage 72APm5211 decreased to 30% of the initial value.

Catheter associated urinary tract infections (CAUTI) pose a serious problem for health care services. The probability of the occurrence of UTI increases by 5% with each additional day of catheterization. After 28 days of catheterization infection is diagnosed in almost 100% of patients [Jacobsen S. M., Stickler D. J., Mobley H. L., Shirtliff M. E.: Complicated catheter associated urinary tract infections due to *Escherichia coli* and *Proteus mirabilis*. Clin. Microbiol. Rev., 2008, 21:26-59]. *P. mirabilis* is isolated from 40% of urine samples from long-term catheterized individuals (over 30 days) [Mobley H T: Virulence of *Proteus mirabilis*. In Urinary tract infections: molecular pathogenesis and clinical management. Edited by Mobley H L, Warren J W. Washington D. C.: ASM Press; 1996:245-270, quoted after Nicolle L. E.: Catheter associated urinary tract infections. Antimicrob. Resist. Infect. Control 2014, 3:23]. Moreover, the activity of urease produced by *P. mirabilis* causes the precipitation of struvite crystals and blocking of the catheter lumen. In consequence, the urine flow is stopped, which might lead to the occurrence of vesicoureteral reflux, resulting in the development of pyelonephritis or even septicemia. *P. mirabilis* is isolated in 80% cases of blocked catheters [Nicolle L. E.: Catheter associated urinary tract infections. Antimicrob. Resist. Infect. Control 2014, 3:23]. In patients requiring long-term catheterization such as those after a stroke, with a damaged spinal cord, suffering from multiple sclerosis or incontinence, *P. mirabilis* infections, especially those caused by drug resistant strains could lead to undesired complications e.g. urinary bladder inflammation, formation of urinary stones, pyelonephritis or bacteriemia.

The economic aspect is not insignificant, either. This aspect is associated with the need of replacing the catheters with the new ones every 8-10 days [Reigstad, C. S., S. J. Hultgren, and J. I. Gordon. 2007. Functional genomic studies of uropathogenic *Escherichia coli* and host urothelial cells when intracellular bacterial communities are assembled. J. Biol. Chem. 282:21259-21267], to allow for delaying the onset of urinary tract infections and adverse effects related thereto. Literature data indicate that annually approximately 5 million patients are undergoing catheterization [Maki, D. G., and Tambyah P. A.: Engineering out the risk for infection with urinary catheters. Emerg. Infect. Dis., 2001; 7: 342-347]. The available sales data allow for an estimation that in the USA more than 30 000 000 urinary catheters are consumed annually, while the incidence of related infections is 10-30% [Darouiche R. O.: Device-associated infections: a macroproblem that starts with microadherence. Clin. Infect. Dis., 2001; 33(9): 1567-72]. Infections related to the use of urinary catheters and consequential complications generate huge costs.

It has now been shown that 39APmC32, 65APm2833 and 72APm5211 bacteriophages of the invention are able to kill planktonic forms of drug-resistant strains of *P. mirabilis*, and also to destruct mature biofilms formed by the species. Under 24 hours incubation at 37° C. in a humidified chamber of 100 μL samples of pure cultures of 50 *P. mirabilis* strains in concentration of $1 \times 10^7$/mL together with 200 pt of phage lysates in concentration of $5 \times 10^5$ pfu/mL of the nutrient broth pH 7.1, comprising 10 mM $MgSO_4$ and 10 mM $CaCl_2$ (the bacteria to phage ratio being 10:1), the tested phages 39A, 65A and 72A inhibited growth of 36, 18 and 35—respectively, out of the 50 *P. mirabilis* strains, to the extent higher than 80%, while the growth of respectively 18, 6 and 17 strains was inhibited to the extent greater than 95% when compared to the control cultures of bacteria grown without the addition of phage lysates. The inhibition of growth of bacteria by phages results in a reduction or lack of biofilm formation on the surface of a polystyrene plate exposed to the bacterial *P. mirabilis* strains. At the same time, other tests also confirmed that a mature 24-hour biofilm formed by the *P. mirabilis* on polystyrene plates is destroyed after 24 hours contact with the bacteriophages of the invention, at concentration of $1 \times 10^7$ pfu/well (phage lysate being prepared in the nutrient broth pH 7.1, comprising 10 mM $MgSO_4$ and 10 mM $CaCl_2$) at 37° C. in a humidified chamber. It has been shown that the phages 39A, 72A and 65A cause greater than 50% reduction of biofilms formed by 31, 28 and 18—respectively, out of the 50 *P. mirabilis* strains, whereas among them the biofilms formed by 11, 15 and 6 strains—resp., are destroyed in more than 75% when compared to the control.

At the same time it should be noted that the bacteriophage proteins—preferably enzymes that degrade bacterial polysaccharides, the enzymes being secreted by the bacteriophages 39A and 72A of the invention additionally are able to decompose bacterial extracellular polysaccharides. The two phages produce plaques surrounded by a zone of halo. It suggests the production of polysaccharide depolymerases by the phages. The polysaccharides are a major component of the matrix of biofilms. As shown above, the two phages 39A and 72A destroy biofilms formed by 31 and 28—resp., strains of *P. mirabilis* in more than 50%, while the phage 65A having a broad host range (positive lytic reactions were observed for 48 tested bacterial strains, and for 39 strains complete lysis of the bacterial lawn was observed), but not forming any halo zone around the plaque, causes eradication of more than 50% the biofilms formed by 18 of the tested strains. These results indicate that the polysaccharide depolymerases produced by the phages 39A and 65A may play an important role in the degradation of the *P. mirabilis* biofilm.

A 35PmC15 phage exhibited an activity in eradication of planktonic forms and biofilms of *P. mirabilis* similar to the activity of the 39A phage, however, in view of the fact that the plaques formed by the aforementioned phage were very small (0.5 mm) and thus it was not possible to obtain reproducible results of its titer determination, it was necessary to exclude the 35PmC15 phage from further studies. In turn, a 66A phage destroyed biofilms of 26 strains to the extent more than 50%, while destroying more than 80% of planktonic forms only of 9 tested strains.

The effectiveness of each and every one of the bacteriophages of the invention in form of a cocktail (mixture) with other phages, against formation and a mature biofilm of *P. mirabilis* was tested. At first, the titer of the 39APmC32, 65APm2833 and 72APm5211 phages within the range from $1\times10^4$ pfu/mL to $1\times10^8$ pfu/mL was determined that was the most efficient in eradication of biofilms formed by three *P. mirabilis*, namely by C71, 3059 and 4107 strains forming biofilms of different susceptibility to phages. In case of the 4107 strain susceptible to the phages, all the tested lysates destroyed the biofilm to the extent of approximately 90%. In turn, biofilms formed by the C71 and 3059 strains, of a low and medium sensitivity to the phages—resp., were subject to eradication to the greatest extent in effect of activity of the phage lysates with the highest titers. The phage preparations with titers equal to $1\times10^7$ pfu/mL were used in further studies. In the studies, binary phage cocktails (39A/65A, 39A/72A and 65A/72A) and the cocktail containing all three phages of the invention were tested. The titer of each phage within a cocktail was $1\times10^7$ pfu/mL, i.e. its titer was the same as in preparations comprising individual phage only. After incubation of liquid cultures and biofilms formed on polystyrene plates with the phages for 24 h at 37° C. in a humidified chamber, viability of bacteria was evaluated using the MTT assay. The cultures with MTT were incubated preferably for 45 minutes at 37° C. in a humidified chamber. The 39A, 65A and 72A bacteriophages and the cocktails very strongly (over 90%) inhibited biofilm formation by 9 of the 16 tested *P. mirabilis* strains. In case of C33, C44, C71 and 3059 bacterial strains, the phages caused reduction of biofilm to the extent of about 30-77%. The formation of biofilm by only one C77 strain was inhibited to the very low extent of 15-30%. A slight interaction of the phages was observed just in case of the 39A/65A phage cocktail and the ternary phage cocktail in inhibiting formation of biofilm by the C44 and C71 strains.

Individual bacteriophages and cocktails exhibited highly differentiated activity against biofilms formed by the tested *P. mirabilis* strains, causing reduction of metabolic activity of the bacteria in the biofilms within the range of about 10-20% to 80-90%. The biofilm formed by C5 strain appears to be resistant to the tested phages. A slight interaction of the phages in biofilm eradication was observed in case of the 39A/65A, 65A/72A phage cocktails and the ternary phage cocktail with respect to the biofilms formed by the C34 and C44 strains.

It has been found that there is no quenching of the activity of the individual bacteriophages of the invention when they are used simultaneously in form of cocktails comprising two and three phage components, except when the cocktails were used against planktonic forms of C33 *P. mirabilis* strain (39A/65A, 65A/72A and the ternary cocktails) and biofilm formed by C77 *P. mirabilis* strain (39A/65A and the ternary cocktails). In those cases the cocktails acted in a way comparable to the least-active component. In the remaining tested systems, the activities of phage cocktails were generally at a similar or slightly higher level in comparison with the activity for most-active phage used alone. There was no clear synergistic effect of individual combinations of the bacteriophages tested, but in a few cases a higher effectiveness of the cocktail, the that of individual bacteriophages was observed, which phenomenon is of great importance for ensuring a complete eradication of the above mentioned biofilm-forming bacteria.

The effectiveness of the bacteriophages of the invention in form of a cocktail (mixture) in combination with antibiotics used in a classic therapy of *P. mirabilis* infections was checked. In the synergism studies the ternary phage cocktail was used in combination with aminoglycoside: amikacin; $3^{rd}$ generation cephalosporin: cefotaxime; and fluoroquinolone: norfloxacin. Biofilms of C8, C15 and C31 *P. mirabilis* strains exhibiting low and medium sensitivity to the phage cocktail were incubated for 24 h at 37° C. in a humidified chamber with the drugs diluted to half their EUCAST breakpoints in the nutrient broth pH 7.1 supplemented with 10 mM $MgSO_4$ and 10 mM $CaCl_2$ and also with the dilutions of the drugs in combination with the phage cocktail wherein a titer of each individual phage was $1\times10^7$ pfu/mL, as well as with the phage cocktail only. After incubation, bacteria viability in the biofilms was assessed by MTT assay, wherein the cultures were incubated with MTT for 45 minutes at 37° C. in a humidified chamber.

Having regard to the EUCAST breakpoints for different drugs, biofilms formed by C8, C15 and C31 *P. mirabilis* were resistant to the drugs tested. It has been observed that in some cases, amikacin and cefotaxime slightly stimulated the biofilm formation. The phage cocktail caused degradation of C31 strain biofilm in about 75%, but it did not destroy biofilms formed by C8 and C15 strains. Synergistic interaction of the phage cocktail and cefotaxime against the biofilms formed by the tested strains was demonstrated. The C31 strain biofilm underwent almost 100% reduction under influence of the phage cocktail and cefotaxime, while the biofilms formed by C8 and C15 strains are destroyed to the extent of about 50% and 75-90%, respectively. No similar interaction was demonstrated for the phage cocktail in combination with amikacin and norfloxacin. In the case of combination of norfloxacin with the phage cocktail, a significant synergistic effect was noted only with respect of biofilms formed by C8 and C15 strains when drug concentration was 256 μg/mL. It was also noted that amikacin and norfloxacin at certain concentrations suppress the activity of the phage cocktail, thus reducing eradication of biofilm. It was found out that cefotaxime ($3^{rd}$ generation cephalosporin) in combination with the phages of the invention—in form of the phage cocktail, has a high potential in destruction of the *P. mirabilis* biofilms.

Product Development

The present invention relates to the development of a product for use in prophylaxis and treatment of infections caused by *P. mirabilis*, as well as in disinfection of facilities and instruments for medical use and for use with respect to food industry. The infections caused by *P. mirabilis*, in which the product shows its effectiveness in prophylaxis and treatment are in particular the urinary tract infections, especially those associated with long-term catheterization and infections of the respiratory tract, eyes, ears, nose, throat, skin, burns, wounds, as well as other infections not listed here. The facilities and instruments for medical use in relation to which the product—as a disinfectant, shows its efficacy in preventing infections caused by *P. mirabilis* are surgery treatment and operating rooms, infirmaries, dispensaries, clinics and urinary catheters of various types, urinary implants such as for example urethra stents. The facilities and instruments for use with respect to food industry in relation to which the product—as a disinfectant, shows its efficacy in preventing infections caused by *P. mirabilis* are slaughterhouses, butcheries, meat factories, grocery stores and the tools used for the raw meat processing.

Use of the product according to the invention can be done by washing or coating the urinary catheters with purified lysates, phage cocktails, or compositions, as well as by coating the catheters and medical implants with neutral hydrogel comprising the phages, phage cocktails or compositions according to the invention. For the purpose of disinfecting facilities, instruments, meat, it is possible to use the phages, phage cocktails or compositions according to the invention in the form of liquids or spray.

The present invention has been illustrated by the following examples:

Example 1. Isolation of Bacteriophages and their Characteristics

Bacteriophages Isolation.

Phages were isolated from the wastewater collected from the Group Sewage Treatment Plant in Lodz and the Station of Water Supply and Sewage in Zgierz using 50 strains of *P. mirabilis*, including 22 strains isolated from biofilms on urological catheters, for which drug susceptibility to 13 antibiotics had been determined [Moryl M., Torzewska A., Jałmużna P. and Różalski A.: Analysis of *Proteus mirabilis* distribution in multi-species biofilms on urinary catheters and determination of bacteria resistance to antimicrobial agents. Pol. J. Microbiol, 2013; 62: 377-384]. 91%, 86% and 82% of these strains were resistant to gentamicin, cotrimoxazole and amoxycillin with clavulanic acid, respectively, and 41% were resistant to ciprofloxacin. Three of the 22 strains showed resistance to all tested drugs. *P. mirabilis* strains derived from the collection owned by the Department of Immunobiology of Bacteria University of Lodz. 22 strains were isolated from catheters obtained from patients of the of the Urological Outpatient Clinic, Pirogow's Hospital in Lodz, the remaining 28 strains came from the urine of patients with UTI treated in the Wards of Neurosurgery, Nephrology, Neurology Rehabilitation, The Children's Memorial Health Institute in Warsaw. Ten mL of wastewater was centrifuged 9000×g, at 4° C. for 30 min., filtered through a sterile filter with a pore diameter of 0.2 μm and mixed with 10 mL 2×conc. TSB (tryptic soy broth) and 1 mL of a 24-hour culture of a suitable *P. mirabilis* strain on TSB. Next, the prepared mixture was shaken 150 rpm/min. for 3 h at 37° C. After incubation about 1 mL of the suspension containing different strains of *P. mirabilis* was spread on a phage nutrient agar plate [Ślopek S., Durlakowa I., Kucharewicz-Krukowska A., Krzywy T., Ślopek A., Weber B.: Phage typing of *Shigella flexneri*. Arch. Immunol. Therap. Exp., 1972; 20(1): 1-60], if the host strain exhibited swarming motility, the phage nutrient agar was supplemented with 0.1% phenol. After harvesting the excess suspension, the plates were incubated for 24 h at 37° C. When added to the medium, phenol prevented swarming of bacteria. A single plaque was cut out with a sterile Pasteur pipette and transferred to nutrient broth and then 50 μL of the 18 h broth culture of the host was added. After 4-hour incubation at 37° C., the cultures were incubated overnight at 4° C. Subsequently, phage lysates were centrifuged 4000 rpm/min, 30 min, at 4° C. on a centrifuge Multifuge 3 S-R Heraeus, and the supernatants were filtered through a sterile filter with a pore diameter of 0.2 μm. The obtained phage lysates were diluted geometrically. From each dilution 200 μL was added to 3 mL of molten nutrient agar (2.8 g agar, 4.2 g of nutrient broth/1000 mL of distilled $H_2O$) containing 100 μL of the 18-hour culture of the host strain, then poured onto a phage nutrient agar plate with or without 0.1% phenol and allowed to solidify. Plates were incubated for 24 hours at 37° C. The procedures for cutting out the plaque and the phage propagation were repeated 5 times to obtain a phage pure line. As a result, 48 phages specific for various *P. mirabilis* strains were obtained (Table 1, below). Phages named 39APmC32, 65APm2833 and 72APm5211 were isolated on *P. mirabilis* strains C32, 2833 and 5211, respectively. For the isolation of 65A and 72A phages, a phage nutrient agar was supplemented with 0.1% phenol. Isolated phages 39APmC32, 65APm2833 and 72APm5211 formed characteristic plaques.

a. Phage 39APmC32 made clear 3 mm, irregular plaques surrounded by halo zones of 5 mm.
b. Phage 65APm2833 made clear plaques with a diameter of 1 mm.
c. Phage 72APm5211 made clear plaques with a diameter of 4 mm surrounded by halo zones of 3 mm.

Determination of the Host Range of the Isolated Bacteriophages.

The spectrum of the lytic activity of the isolated phages was determined using 50 uropathogenic *P. mirabilis* strains described above. Six mL of molten nutrient agar containing 150 μL of a 20-hour culture of each bacterial strain was poured on a phage nutrient agar plate and, when the agar solidified, 10 μL of the phage lysate with the number of viral particles $1×10^8$ pfu/mL was applied. The titer of the phage was determined by the Gratia method. The plates were incubated for 4 h at 37° C., then overnight at 4° C. The degree of lysis of the bacterial layer was defined using a 1-4 scale, taking into account the presence of single plaques in the area where the phage lysate was dropped, wherein 4 was considered as complete bacterial lysis on the spot, 3—almost clear spot, 2—medium bacterial lysis on the spot, 1—weak bacterial lysis on the spot Mutter E.: Phage host range and efficiency of plating. In Clokie M R J, Kropinski A M (Eds): Bacteriophages: methods and protocols. Volume 1: Isolation, characterization, and interactions. Vol. 501, Humana Press, New York, 2009; p. 141-149]. The results are presented in Table 2. The phages selected for the patent application were characterized by the following lytic reactions:

a. Bacteriophage 65A—positive lytic reactions were observed for 48 strains tested, including 39 (4) 5 (3) 3 (2) 1 (1).
b. Bacteriophage 39A—positive lytic reactions were observed for 46 strains tested, 20 (4), 6 (3), 11 (2), 8 (1) and 1—single plaques.
c. Bacteriophage 72A—positive lytic reactions were observed for 34 strains tested, 21 (4) 3 (3) 6 (2), 4 (1).

Examination of Bacteriophages Morphology Using an Electron Microscope.

For phages numbered 39APmC32, 65APm2833 and 72APm5211 the pictures were taken by an electron microscope JEOL 1010 TEM at 80 kV. For this purpose, 1 mL of phage lysate with a titer of $1.67×10^{10}$ pfu/mL to $1.95×10^{10}$ pfu/mL was centrifuged 24 500×g for 3 h at 4° C. Then, while maintaining the above conditions for centrifugation, the pellet was washed twice with 5% ammonium molybdate solution, pH 6.0. Phages remaining in the sediment were suspended in 15 μL of 5% ammonium molybdate to obtain the titer of $10^{11}$ pfu/mL. Subsequently, 7.5 μL of the phage suspension was applied to the formvar and carbon coated copper gird, and left for 5 minutes on the filter paper to absorb the sample. The preparations were then stained with 2% uranyl acetate for 1 min. and viewed under a microscope.

All viewed bacteriophages have a polyhedral head and tail, indicating that they belong to the order Caudovirales (FIG. 1). In the preparations of phages 39APmC32 and 65APm2833 a virus with a contracted tail was observed.

This points to the fact that these phages belong to the Myoviridae family. In the preparation of phage 72APm5211, only virions with long, uncontracted tails were detected, which were probably the representatives of the family Siphoviridae.

Preliminary Molecular Characterization—RFLP.

Figure 2:
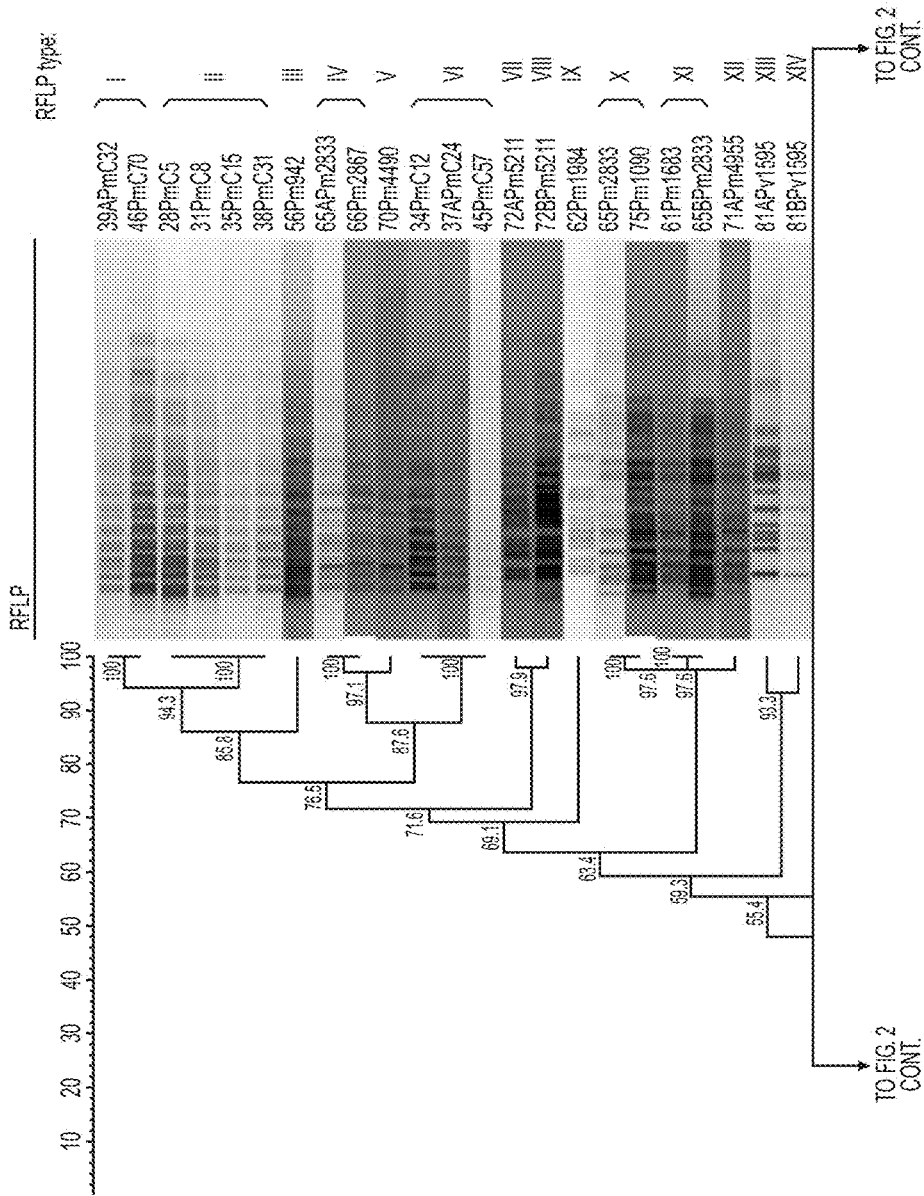
FIG. 2 presents a dendrogram showing the similarity of 51 *Proteus* specific bacteriophages isolated in accordance with the invention; analysis of the restriction profiles obtained after the digestion of phage DNA with EcoRV, allowed classifying 51 phages into 34 characteristic EcoRV RFLP-types numbered from I to XXXIV; % similarity is marked on the dendrogram (Dice similarity index)
Figure 2:
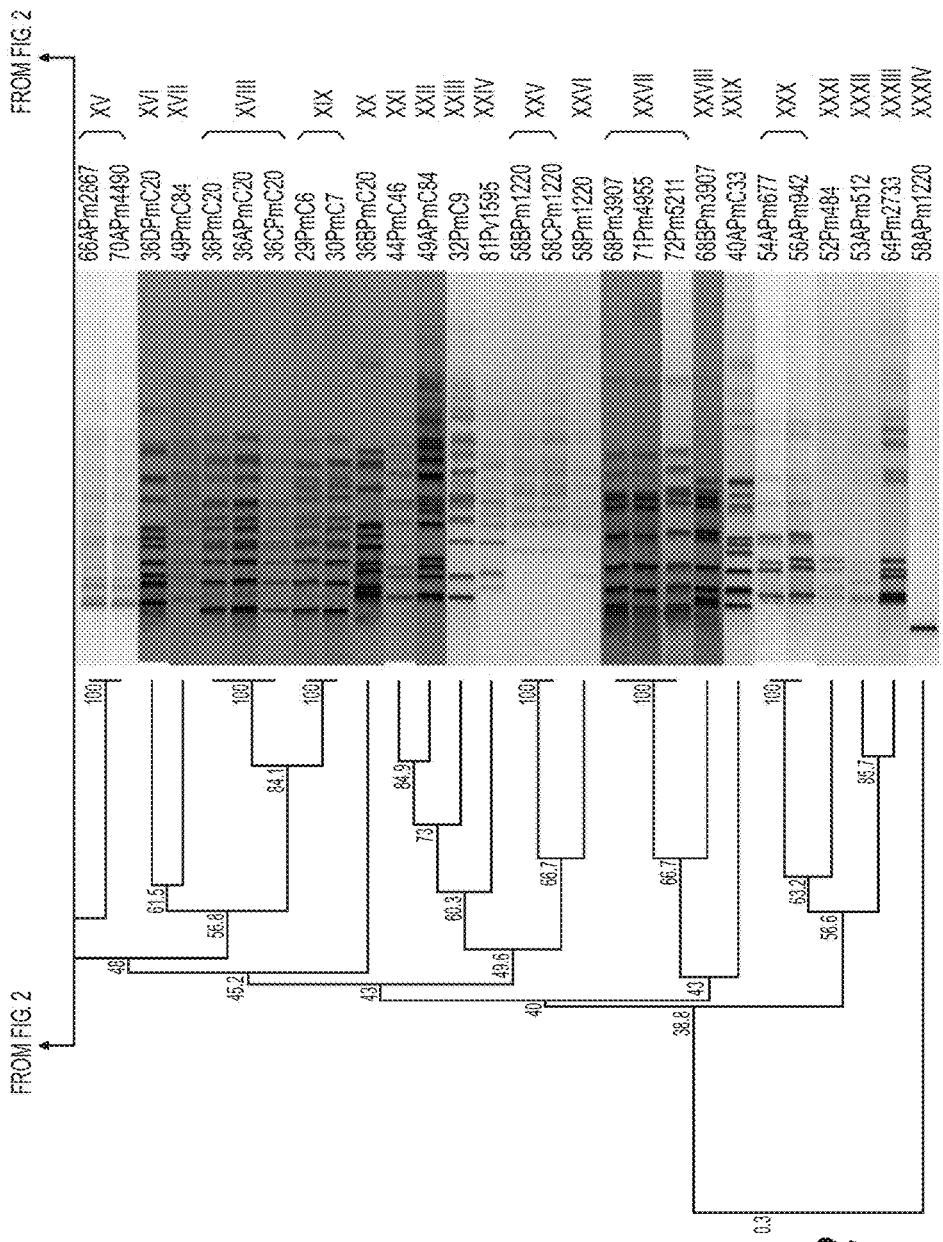

In order to provide the initial molecular characterization of the isolated phages (three phages specific for *Proteus vulgaris* 1595-81Pv1595, 81APv1595 and 81BPv1595 were used additionally), particularly viruses 39APmC32, 65APm2833 72APm5211, their DNA was isolated by the modified Su et al. method [Su M T, Tyamagondlu V. V., Bodmer R.: Large- and small-scale preparation of bacteriophage lambda lysate and DNA. BioTechniques, 1998; 25(1): 44-46] and digested with EcoRV. The obtained restriction profiles specific to particular phages allowed for the differentiation of isolated phages, verification if the isolated phages were duplicated by the isolation of the same virus using different host strains and the initial molecular assessment of the phages (FIGS. 1 and 2).
  a. It has been shown that phage 39A is identical with the phage designated as 46PmC70 and 94.3% similar to phages 28PmC5, 31PmC8, and 35PmC15 38PmC31.
  b. It has been shown that phage 65A is identical with the phage designated as 66Pm2867 and 97.1% identical to phage 70Pm4490.
  c. It has been shown that phage 72A is identical in 97.9% with phage 72BPm5211.

Determination of Phage Susceptibility to Temperature, pH of the Environment and Chloroform.

Phage lysates ($1\times10^7$ pfu/mL) were incubated for 30 and 60 min at 50° C., 60° C., 70° C., 80° C. Control phages were incubated at 37° C. After the incubation the lysates were cooled to room temperature and phage titers were determined by the double agar overlay method. In order to investigate the bacteriophages sensitivity to pH, sterile PBS buffers were prepared (0.015 M $Na_2HPO_4xH_2O$, 0.15 M NaCl) at pH 2, pH 4, pH 5, pH 6, pH 7, pH 8, pH 10 and a control buffer at pH 7.5. 100 µL of phage lysate was added to 900 µL of each buffer ($1\times10^7$ pfu/mL) and incubated for 1 h in a water bath at 37° C. Then, using 0.4 M NaOH or 3.7% HCl the pH of each sample was adjusted to neutral pH. Titers of bacteriophages in the examined samples were determined by the double agar overlay method.

The effect of chloroform on the phages was examined by a 2-hour incubation of 0.5 mL of phage lysate ($1\times10^7$ pfu/mL) with 0.5 mL of chloroform at room temperature. Every 15 minutes, the tubes contents were vigorously mixed. After incubation, the samples were centrifuged 10 000 rpm, 10 minutes at room temperature and the aqueous phase was collected into sterile tubes. Titers of the phages in the samples were determined by the Gratia assay.

Figure 3A:
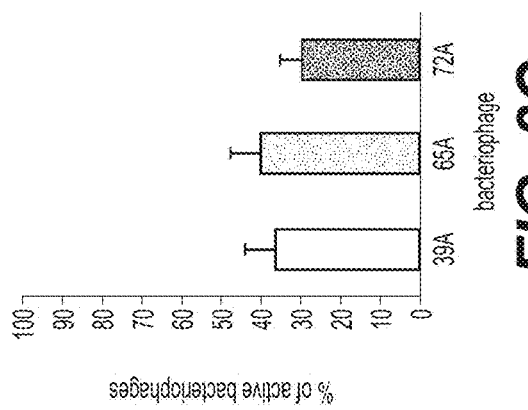
FIGS. 3A to 3C present the effects of physicochemical factors: A) temperature, B) pH of the medu and C) chloroform on the bacteriophages of the invention; 39APmC32=39A, 65A=65APm2833, 72A=72APm5211.

Bacteriophages 65A and 72A retained activity at a similar level in the range of pH 4 to 7, and 39A in the range of pH 5 to 7 (FIG. 3A). pH 2 and 12 completely deactivated the phages. Phage titers 65A and 72A decreased to 70% and 59% after incubation in PBS pH 8 and 10, respectively. The activity of phage 39A dropped to about 65% after incubation in PBS pH 4 and 8 and to 35% at pH 10.

Figure 3B:
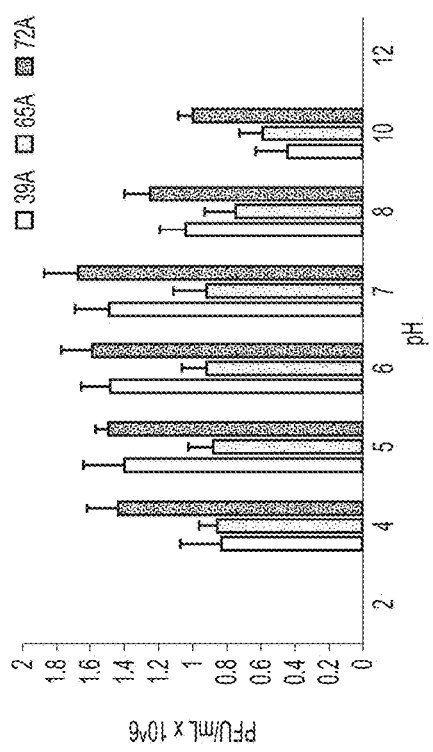

Bacteriophages incubated at 37° C. were used as virus activity control (FIG. 3B). Bacteriophages 65A and 72A retained their activity after incubation at 50° C., independently of the incubation time. The incubation of phages at 60° C. for 0.5 h decreased their activity to 55%, and the incubation for 1 h to about 30-35% of control activity. The incubation at 50° C. for 0.5 h decreased the activity of phage 39A to 77%, and for 1 h to 50% compared to control. The incubation of phage 39A at 60° C. for 0.5 h reduced its activity to 37% and for 1 h to 12%. The tested phages totally lost their activity at the temperatures 70 and 80° C.

Figure 3C:
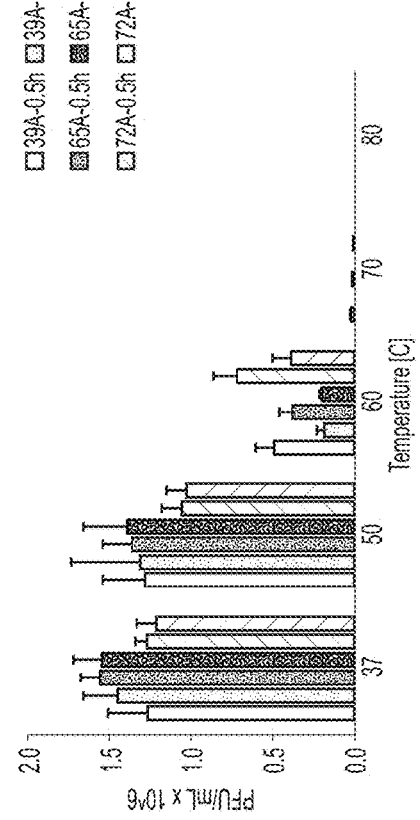

The results presented in FIG. 3C show that 50% chloroform resulted in a decrease in the titer of bacteriophages 39APmC32 and 65APm2833 to about 40%, and the 72APm5211 phage titer decreased to 30% of the initial value.

Example 2. Examination of *P. mirabilis* Biofilms Sensitivity to the Isolated Phages Fifty *P. mirabilis* strains were used, including 22 strains isolated from the biofilm formed on the urological catheters and 28 from the urine samples of patients with UTI. Bacterial cultures incubated for 20 h at 37° C. was diluted 50-fold in nutrient broth pH 7.1 to a final titer of about $1\times10^7$/mL. Bacterial cultures were applied onto a 96-well flat bottom polystyrene plate in a volume of 100 µL per well. After 24 hours of incubation at 37° C. in a humidified chamber, the medium was collected and bacterial biofilms were washed with sterile 0.85% NaCl. Next, 100 µL phage lysates at the titer $1\times10^8$ pfu/mL of nutrient broth pH 7.1 supplemented with 10 mM $MgSO_4$ and 10 mM $CaCl_2$ were added to appropriate wells. Phage suspensions and nutrient broth pH 7.1 supplemented with 10 mM $MgSO_4$ and 10 mM $CaCl_2$, which were background control, were added to the other wells. Bacterial cultures untreated with phages, to which nutrient broth pH 7.1 supplemented with 10 mM $MgSO_4$ and 10 mM $CaCl_2$ was added, were considered as control of *P. mirabilis* biofilm formed by particular strains. Plates were incubated for 24 h at 37° C. in a humidified chamber. After incubation, the wells were washed with sterile 0.85% NaCl and 100 µL of nutrient broth pH 7.1 containing 10 mM $MgSO_4$ and 10 mM $CaCl_2$ and 10 µL of MTT [3-(4,5-dimethyl-2-yl)-2,5 diphenyltetrazolium bromide] at 5 mg/mL PBS were added. After 3-hour incubation at 37° C. in a humidified chamber, the medium was collected and to each well 150 µL of DMSO and 25 µL of glycine buffer pH 10.6 (50 mL of 0.2 M glycine, 43.5 mL of 0.2 M NaOH, 106.5 mL of bidistilled water) were added to dissolve the formazan crystals. The absorbance value was measured at a wavelength of 550 nm on a plate reader Labsystems Ex Multiscan type 355. From the absorbance values of each tested sample the background value was subtracted, which was the absorbance value obtained for the control phage and nutrient broth pH 7.1 supplemented with 10 mM $MgSO_4$ and 10 mM $CaCl_2$. The percentage of *P. mirabilis* biofilm reduction caused by the phages was calculated using the formula: % of biofilm destruction=100%−($A_{S550}\times100\%/A_{CB550}$), wherein: $A_{S550}$—was the average value of absorbance at 550 nm of the tested sample–biofilm treated with phage; $A_{CB550}$—the average value of absorbance at 550 nm of biofilms grown in nutrient broth pH 7.1 supplemented with 10 mM $MgSO_4$ and 10 mM $CaCl_2$ without the addition of phages. The results are presented in Table 3 below.

It has been shown that phage 39A caused an over 50% biofilm reduction in 31 of the 50 *P. mirabilis* strains studied, whereas biofilms of 11 strains were destroyed by more than 75% compared to control. Phage 72A caused an over 50% biofilm reduction in 28 of the 50 *P. mirabilis* strains, whereas biofilms of 15 strains were destroyed by more than 75% compared to control. Phage 65A led to an over 50% biofilm destruction in 18 of the 50 P. mirabilis strains, including the biofilms of 6 strains which were destroyed by more than 75% compared to control.

Example 3. Study of the Planktonic Forms of P. mirabilis Sensitivity to Phages Fifty P. mirabilis strains were used, including 22 strains isolated from the biofilm formed on urinary catheters and 28 from urine samples of patients with UTI. Bacterial cultures incubated for 20 h at 37° C. were diluted 50-fold in nutrient broth pH 7.1 to a final titer of about $1 \times 10^7$/mL. 100 μL bacterial cultures per well were inoculated onto a 96-well flat bottom polystyrene plate. The 200 μL/well of phage lysate with a titer of $5 \times 10^5$ pfu/mL of nutrient broth pH 7.1 containing 10 mM $MgSO_4$ and 10 mM $CaCl_2$ was added. Phage lysates and nutrient broth pH 7.1 supplemented with 10 mM $MgSO_4$ and 10 mM $CaCl_2$, which were the background control were added to separate wells. Cultures of P. mirabilis strains untreated with phages, to which nutrient broth pH 7.1 supplemented with 10 mM $MgSO_4$ and 10 mM $CaCl_2$ were added, constituted the control of bacterial growth. After 24 h incubation at 37° C. in a humid chamber, the absorbance of samples was measured at a wavelength of 550 nm on a plate reader Labsystems Ex Multiscan type 355. The background value, which was the absorbance value obtained for the control phage and nutrient broth pH 7.1 supplemented with 10 mM $MgSO_4$ and 10 mM $CaCl_2$, was subtracted from the absorbance values of the particular tested samples. The percentage of P. mirabilis planktonic forms growth reduction caused by the phages was calculated using the formula: % of growth reduction=100%−($A_{S550} \times$ 100%/$A_{CG550}$), wherein: $A_{S550}$—was the average value of absorbance at 550 nm wavelength of the tested sample—liquid cultures treated with phages; $A_{CG550}$—the mean absorbance value at 550 nm in a liquid culture in nutrient broth pH 7.1 supplemented with 10 mM $MgSO_4$ and 10 mM $CaCl_2$ without phages. The results are presented below in Table 4.

It has been shown that phage 39A inhibited growth by more than 80% in 36 of the 50 P. mirabilis strains tested, whereas the growth of 18 strains was inhibited by over 95% compared to control. Phage 65A inhibited growth by more than 80% in 18 of the 50 P. mirabilis strains, including growth inhibition in the case of 6 strains by more than 95% compared to control. Phage 72A inhibited growth by more than 80% in 35 of the 50 P. mirabilis strains, whereas the growth of 17 strains was inhibited by more than 95% compared to control.

Example 4. Study of the Phage Cocktail Influence on Biofilm Formation and the Mature P. mirabilis Biofilm In the study 16 uropathogenic P. mirabilis strains and preparations containing single phages 39A, 65A and 72A, two-component phage cocktails: 39A/65A, 39A/72A and 65A/72A and a cocktail consisting of three tested phages were used. The titers of particular phages in the formulations were $2 \times 10^7$ pfu/mL and $1 \times 10^7$ pfu/mL for investigating the effect of phages on biofilm formation and mature biofilm, respectively. In order to study the effect of the phage cocktails on biofilm formation 50 μL of phage preparations was added to each well. Next, 50 μL of nutrient broth pH 7.1 with 10 mM $Ca^{2+}$ and $Mg^{2+}$ was added to each of the biofilm control wells, which after bacteria addition was accepted as 100% control of biofilm formation. Then, 50 μL samples of 18-hour, 25-fold diluted cultures of 16 P. mirabilis strains were added in triplicate to appropriate wells.

After 24 h incubation at 37° C. in a humid chamber, the bacterial viability was assessed using the MTT method, where the time of incubation was 45 minutes. In order to initiate biofilm formation, 100 μL of a 18-hour P. mirabilis culture diluted 50-fold in nutrient broth pH 7.1 was inoculated onto a 96-well flat-bottom polystyrene plate and incubated for 24 h at 37° C. in a humidified chamber. After incubation, the medium was collected from the the biofilm and the wells were washed with 100 μL of sterile 0.85% NaCl.

Then, 100 μL of phage preparation in triplicate was added to each well. Phage preparations and nutrient broth pH 7.1 were applied to the control wells and constituted sterility and background control. Biofilms grown in a nutrient broth were 100% control of biofilms formation. After 24 h incubation at 37° C. in a humid chamber, the bacterial viability was assessed using the MTT method, where the time of incubation was 45 minutes. The percentage of P. mirabilis biofilm reduction caused by the phages was calculated using the formula: % of biofilm destruction=100%−($A_{S550} \times 100\%$/$A_{O3550}$), wherein: $A_{S550}$—was the average value of absorbance at 550 nm of the tested sample-biofilm and planktonic culture treated with phages, $A_{O3550}$—the average value of absorbance at 550 nm of biofilms grown in nutrient broth pH 7.1 containing 10 mM $MgSO_4$ and 10 mM $CaCl_2$ without the addition of the phage. The results are presented in FIG. 4 and FIG. 5.

Figure 4:
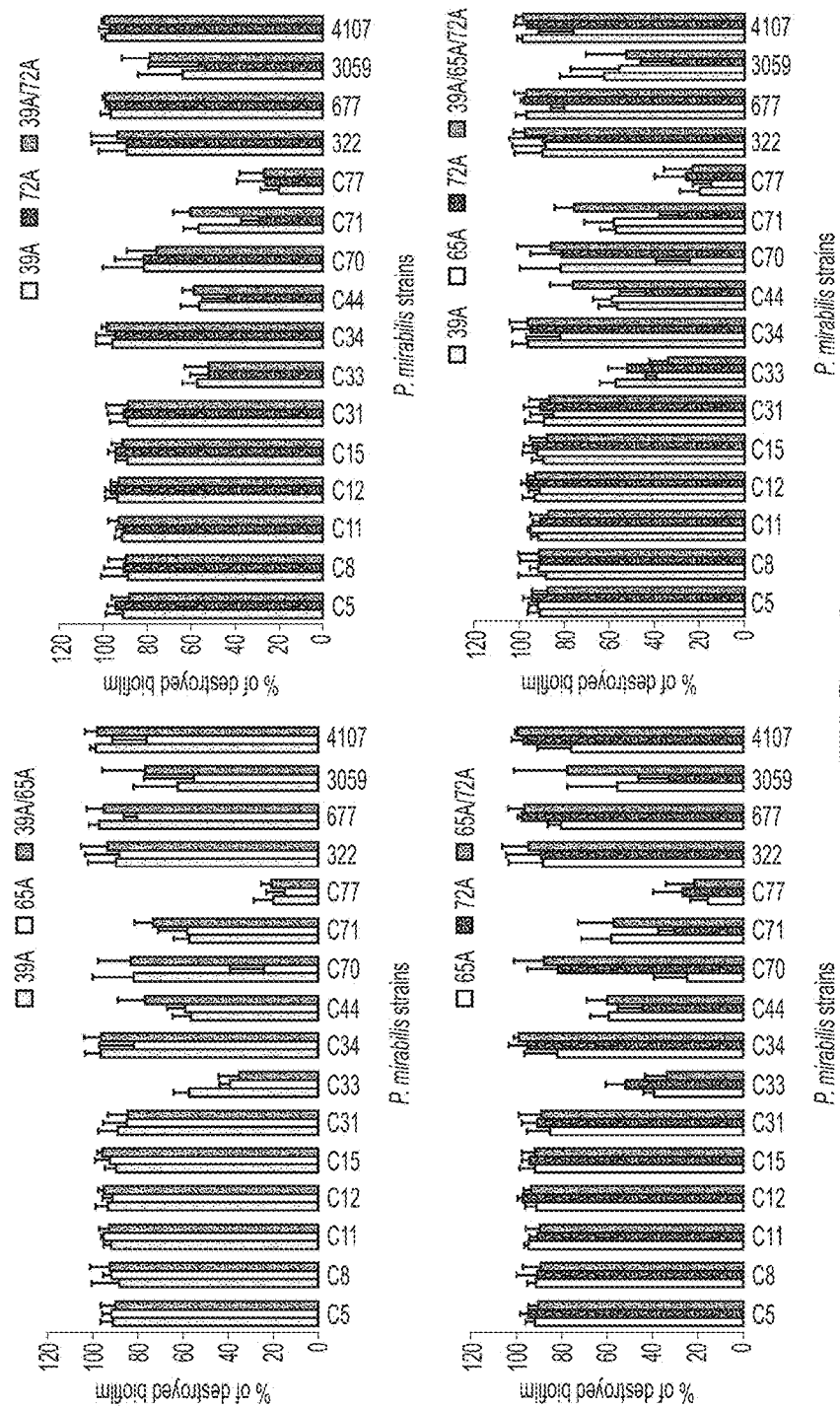
FIG. 4 shows the effects of the bacteriophages of the invention and phage cocktails on *P. mirabilis* biofilm formation; 39APmC32=39A, 65A=65APm2833, 72A=72APm5211.

The bacteriophages 39A, 65A and 72A and the used phage cocktails, mostly very strong (even over 90%), inhibited the biofilm formation by the examined P. mirabilis strains (FIG. 4). The strains C33, C44, C71, C77 and 3059 in the case of which the biofilm reduction reached about 20-80% were an exception. No synergistic inhibiting activity of the phages on the process of biofilm formation was observed. The inhibition of biofilm formation by phage cocktails was on the level similar to the inhibition of biofilm formation by single phages with the strongest activity. It is worth mentioning that phages in a cocktail did not inhibit each other's activity.

Figure 5:
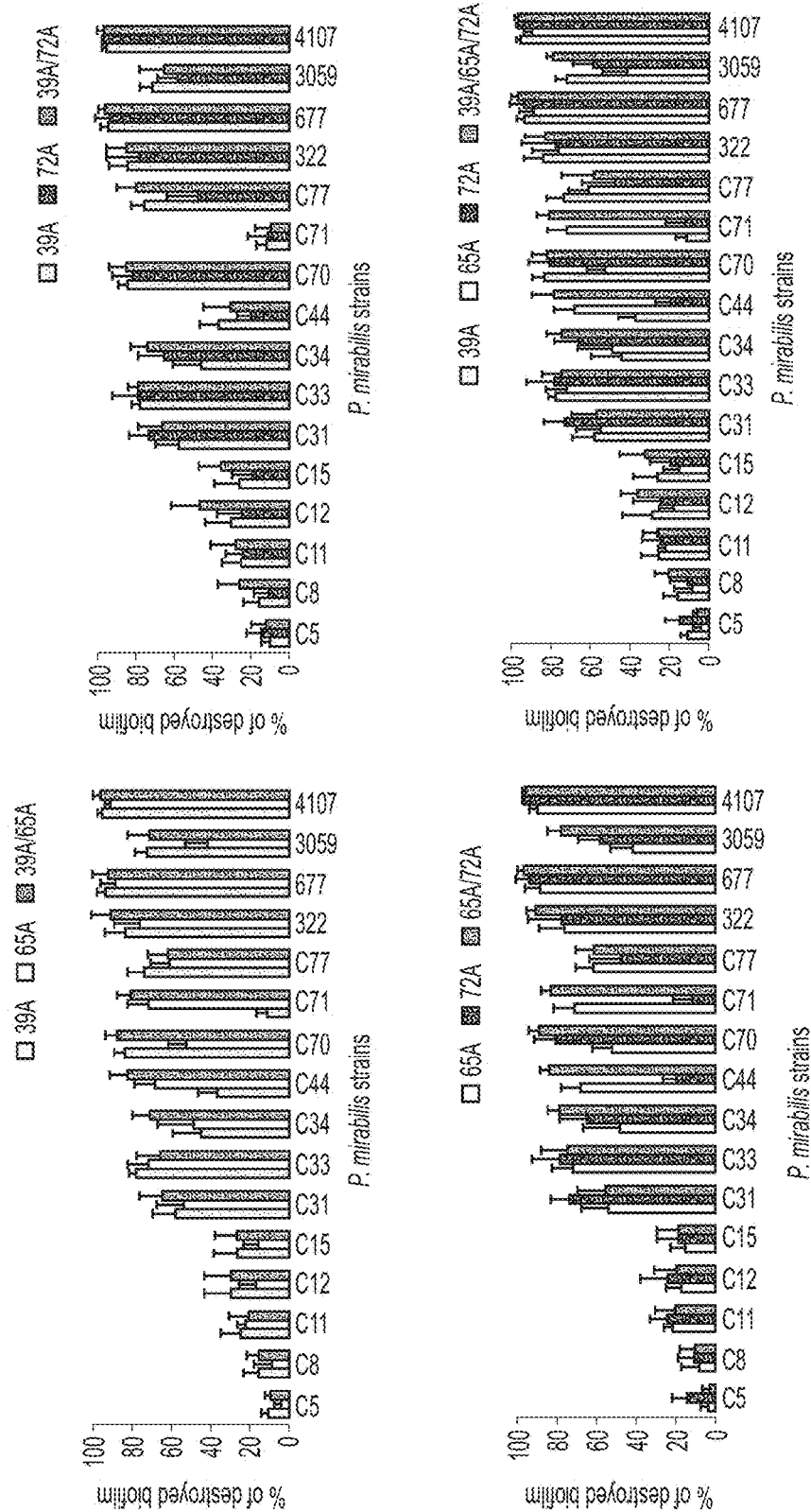
FIG. 5 presents the effects of the bacteriophages of the invention and phage cocktails on mature biofilm of *P. mirabilis;* 39APmC32=39A, 65A=65APm2833, 72A=72APm5211.

Biofilms formed by the tested P. mirabilis strains showed high differentiation in susceptibility to phage preparations (FIG. 5). The decrease in metabolic activity of bacteria in biofilms treated with phages in different combinations ranged from 10-20% to 80-90%, depending on the tested strain. The biofilms reduction by the two- or three-component phage cocktails used was equal to or slightly higher than the biofilm reduction caused by the strongest acting on the biofilm phage. It is very important that used phages did not inhibit each other's activity, when used in a cocktail. This is of great practical importance, because phage cocktails are characterized by a broader range of sensitive hosts than single phages.

Figure 6:
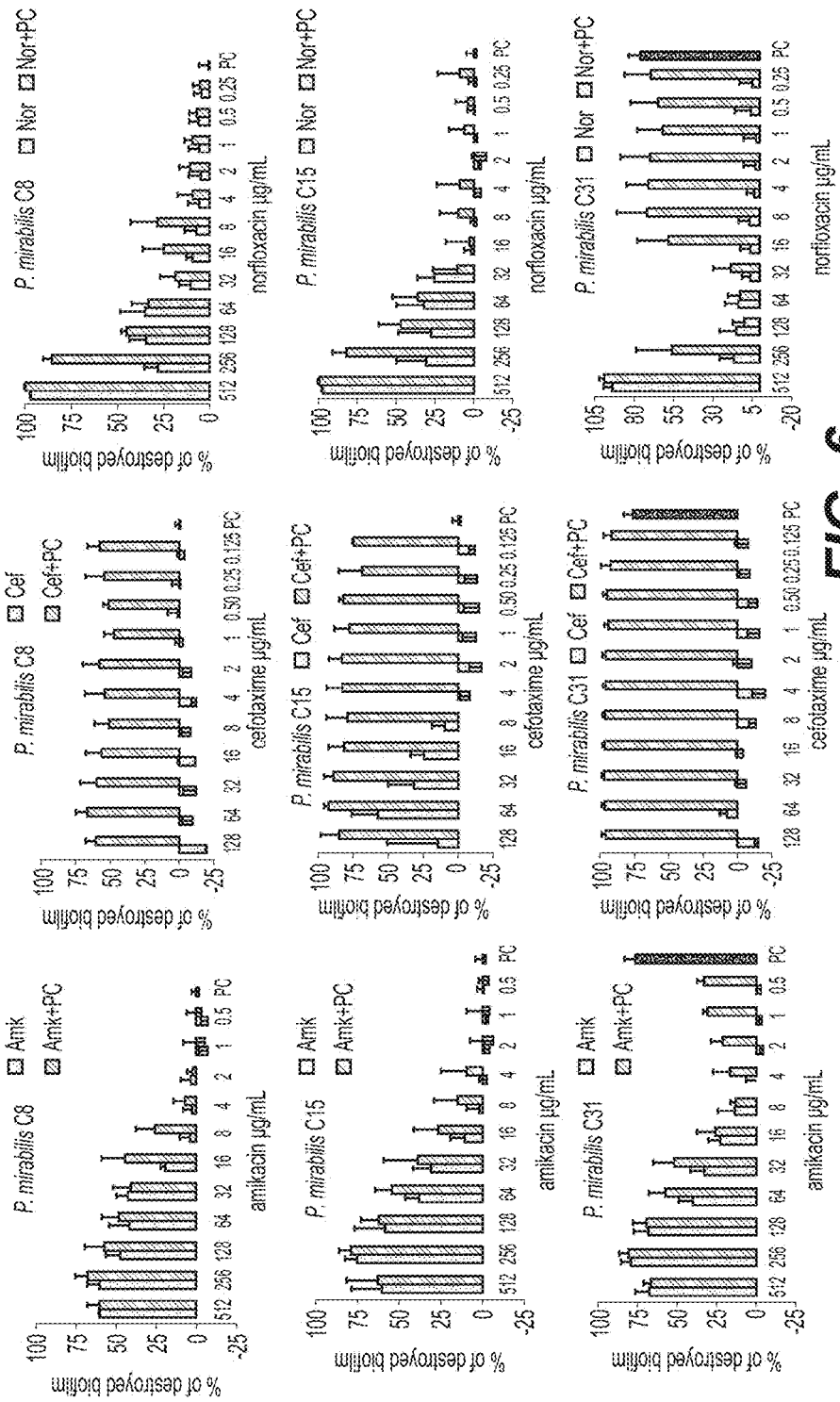
FIG. 6 presents the common action of the phage cocktail containing 39APmC32, 65APm2833, 72APm5211 phages with amikacin, cefotaxime or norfloxacin in *P. mirabilis* biofilm eradication.
Figure 8:
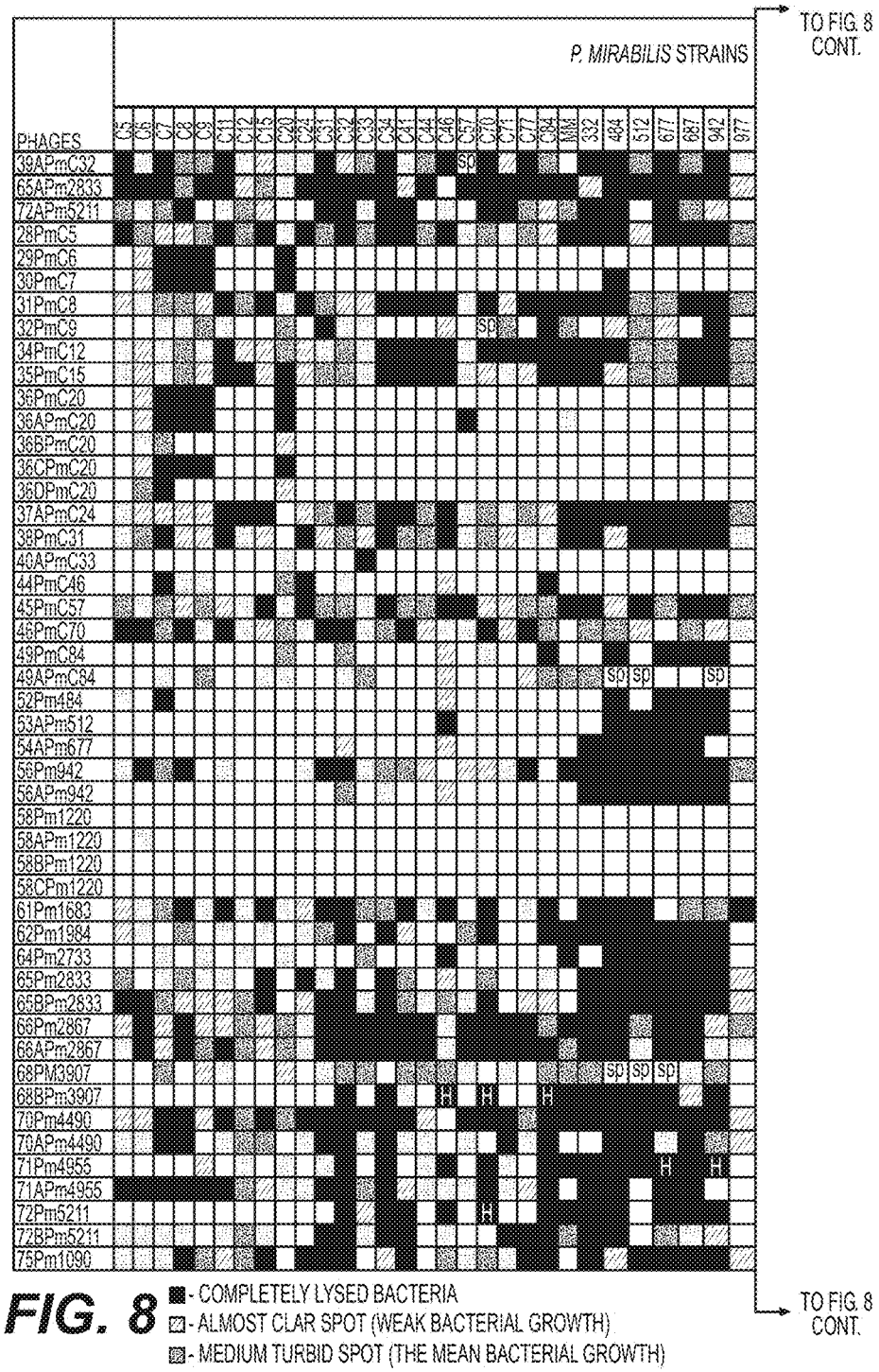
FIG. 8 presents Table 2.

Example 5. Examination of the Synergism of Selected Drugs with a Phage Cocktail in P. mirabilis Biofilm Eradication Amikacin (an aminoglycoside), cefotaxime (a $3^{rd}$ generation cephalosporin) and norfloxacin (fluoroquinolone) were used to study their synergism with a phage cocktail containing phages 39A, 65A i 72A. 100 μL samples of 50-fold diluted 18h cultures of P. mirabilis strains C8, C15 and C31 with low or medium sensitivity to the phage cocktail activity were inoculated onto a 96-well polystyrene plate. After 24h incubation at 37° C. the biofilms were washed with 100 μL of 0.85% NaCl. Next, a number of dilutions of particular drugs were performed in a nutrient broth pH 7.1 containing 10 mM $MgSO_4$ and $CaCl_2$ directly on the plate with biofilm. Norfloxacin was diluted in the geometric progression from 512 µg/mL to 0.25 µg/mL, amikacin from 512 µg/mL to 2 µg/mL and cefotaxime from 128 µg/mL to 0.5 µg/mL in the final volume of 100 µL to obtain the drugs concentration of half their EUCAST breakpoints for determining bacterial sensitivity according to the EUCAST norms. In the same way the drugs were diluted at two-fold higher concentrations in the volume of 50 µL, to which 50 µL of the phage cocktail with the phages titer $2 \times 10^7$ pfu/mL was added to obtain the same final concentration of the antibiotics in both dilution systems. Bacterial biofilm cultured in nutrient broth constituted 100% of biofilm control. The phages, antibiotics and nutrient broth added to the sterile wells were accepted as sterility and background controls. An additional control was phages treated biofilm. The final volume in all wells was 100 µL. After 24h incubation at 37° C. in a humidified chamber, the viability of the bacteria was assessed using the MTT assay, where the incubation time was 45 minutes. The results are presented in FIG. 6.

Taking into consideration the EUCAST breakpoints, the biofilms formed by *P. mirabilis* strains C8, C15 and C31 were resistant to the activity of the drugs used. On the other hand, the phage cocktail caused strain C31 biofilm eradication by about 75% but it did not destroy biofilms formed by strains C8 and C15. The synergistic activity of the phage cocktail with cefotaxime against the biofilms of all tested strains was revealed. In the case of the biofilm formed by strain C31, the phage cocktail in connection with cefotaxime caused an almost 100% biofilm reduction, and the biofilms formed by strains C8 and C15 were destroyed on the levels 50% and 75-90%, respectively. No similar cooperation with the phage cocktail was shown for amikacin or norfloxacin. In the case of fluoroquinolone, a noticeable synergistic action with the phage cocktail was observed only against the biofilms formed by strains C8 and C15 at the drug concentration 256 µg/mL.

The invention claimed is:

1. An antibacterial composition comprising a derivative of at least one bacteriophage strain specific against bacteria belonging to the species *Proteus mirabilis*, wherein the at least one bacteriophage strain is selected from the group consisting of bacteriophage deposited with the Polish Collection of Microorganisms (PCM) under the access numbers: F/00084 (72APm5211), F/00085 (39APmC32), and F/00086 (65APm2833).

2. The antibacterial composition of claim 1, wherein the derivative of the at least one bacteriophage strain comprises bacteriophage lysate or a purified bacteriophage protein.

3. The antibacterial composition of claim 2, wherein the purified bacteriophage protein is selected from lytic enzymes that degrade the bacterial cell wall and enzymes that decompose bacterial extracellular polysaccharides.

4. The antibacterial composition of claim 1, wherein the composition comprises a derivative of each of two or more active bacteriophages.

5. A method for prophylaxis and combating an infection caused by bacteria belonging to the species *P. mirabilis*, comprising administering an antibacterial composition comprising at least one bacteriophage strain specific against bacteria belonging to the species *Proteus mirabilis* or a derivative of the at least one bacteriophage strain, wherein the at least one bacteriophage strain is selected from the group consisting of bacteriophage deposited with the Polish Collection of Microorganisms (PCM) under the access numbers: F/00084 (72APm5211), F/00085 (39APmC32), and F/00086 (65APm2833).

6. The method of claim 5, wherein the infection is within the urinary tract.

7. The method of claim 5 wherein the antibacterial composition is administered in combination or in composition with other medicaments or anti-bacterial agents.

8. A method for the disinfection of a surface or instrument, comprising contacting the surface or instrument with an antibacterial composition comprising at least one bacteriophage strain specific against bacteria belonging to the species *Proteus mirabilis* or a derivative of the at least one bacteriophage strain, wherein the at least one bacteriophage strain is selected from the group consisting of bacteriophage deposited with the Polish Collection of Microorganisms (PCM) under the access numbers: F/00084 (72APm5211), F/00085 (39APmC32), and F/00086 (65APm2833).

9. The method of claim 8, wherein the instrument is a medical device or an instrument for use in food preparation.

10. The method of claim 9, wherein the instrument is for use in the production or preparation of meat products.

11. The method of claim 5, wherein the antibacterial composition is administered as a spray, compress, rinse/wash liquid preparation or wet compress.

12. The method of claim 5, wherein the antibacterial composition is administered as a gel form.

13. The method of claim 8, wherein the antibacterial composition is administered as a spray, compress, rinse/wash liquid preparation or wet compress.

14. The method of claim 8, wherein the antibacterial composition is a gel form.

15. The method of claim 5, wherein the derivative of the at least one bacteriophage strain comprises bacteriophage lysate or a purified bacteriophage protein.

16. The method of claim 15, wherein the purified bacteriophage protein is selected from lytic enzymes that degrade the bacterial cell wall and enzymes that decompose bacterial extracellular polysaccharides.

17. The method of claim 8, wherein the derivative of the at least one bacteriophage strain comprises bacteriophage lysate or a purified bacteriophage protein.

18. The method of claim 17, wherein the purified bacteriophage protein is selected from lytic enzymes that degrade the bacterial cell wall and enzymes that decompose bacterial extracellular polysaccharides.

19. The method of claim 9, wherein the medical device is a urologic catheter.

20. The method of claim 19, wherein the antibacterial composition is a gel form.

* * * * *